US012740842B2

(12) United States Patent
Chaplin et al.

(10) Patent No.: US 12,740,842 B2
(45) Date of Patent: Sep. 22, 2026

(54) ROBOTIC SURGICAL INSTRUMENT

(71) Applicant: CMR SURGICAL LIMITED, Cambridge (GB)

(72) Inventors: Ben Robert Chaplin, Cambridge (GB); Dominic Martin McBrien, Cambridge (GB); Gareth Stephen Hearn, Centennial, CO (US); Simon Roderick Grover, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 205 days.

(21) Appl. No.: 18/580,428

(22) PCT Filed: Jul. 18, 2022

(86) PCT No.: PCT/GB2022/051845
§ 371 (c)(1),
(2) Date: Jan. 18, 2024

(87) PCT Pub. No.: WO2023/002164
PCT Pub. Date: Jan. 26, 2023

(65) Prior Publication Data

US 2025/0072987 A1 Mar. 6, 2025

(30) Foreign Application Priority Data

Jul. 19, 2021 (GB) ..................................... 2110380

(51) Int. Cl.
*A61B 34/00* (2016.01)
*A61B 34/30* (2016.01)

(52) U.S. Cl.
CPC ........ *A61B 34/71* (2016.02); *A61B 2034/302* (2016.02); *A61B 2034/305* (2016.02)

(58) Field of Classification Search
CPC ................ A61B 18/1442; A61B 34/71; A61B 2034/305
See application file for complete search history.

(56) References Cited

U.S. PATENT DOCUMENTS

| | | | |
|---|---|---|---|
| 5,807,378 | A | 9/1998 | Jensen et al. |
| 10,792,113 | B2 | 10/2020 | Cuthbertson et al. |

(Continued)

FOREIGN PATENT DOCUMENTS

| | | | |
|---|---|---|---|
| EP | 3845155 | A1 | 7/2021 |
| GB | 2563233 | A | 12/2018 |
| WO | 2017098273 | A1 | 6/2017 |

OTHER PUBLICATIONS

Notification of Transmittal of the International Search Report and the Written Opinion of the International Searching Authority from corresponding PCT/GB2022/051842 dated Oct. 17, 2022.

(Continued)

*Primary Examiner* — Allen Porter
(74) *Attorney, Agent, or Firm* — Lando & Anastasi, LLP

(57) ABSTRACT

There is provided a robotic surgical instrument comprising an end effector, a shaft component, a supporting body, a pulley, and a protrusion. The supporting body is connected to a distal end of the shaft component at a first end and to the end effector at a second end. The supporting body comprises first and second flanges extending from the first end into the shaft component. The pulley faces an outer surface of the first flange. The protrusion is coupled to the distal end of the shaft component and extends towards the end effector. The protrusion is configured to interface with an interfacing surface of one of the first or second flanges when the supporting body is moved towards the pulley. The separation between the outer surface of the first flange and the pulley (Continued)

is greater than the separation between said interfacing surface of one of the first or second flanges and the protrusion.

20 Claims, 8 Drawing Sheets

(56) References Cited

U.S. PATENT DOCUMENTS

| | | | | |
|---|---|---|---|---|
| 2003/0208186 | A1 | 11/2003 | Moreyra | |
| 2007/0299427 | A1 | 12/2007 | Yeung et al. | |
| 2016/0310156 | A1* | 10/2016 | Kapadia | A61B 17/295 |
| 2019/0282291 | A1 | 9/2019 | Worrell et al. | |
| 2020/0093468 | A1 | 3/2020 | Chaplin et al. | |
| 2020/0138510 | A1 | 5/2020 | Grover | |
| 2020/0138531 | A1 | 5/2020 | Chaplin | |
| 2020/0197109 | A1* | 6/2020 | Chaplin | B25J 9/1045 |
| 2020/0405424 | A1* | 12/2020 | Schuh | A61B 34/71 |
| 2021/0196416 | A1 | 7/2021 | Betsugi et al. | |
| 2021/0298849 | A1* | 9/2021 | Ago | A61B 17/3201 |
| 2023/0380918 | A1* | 11/2023 | Wang | A61B 34/37 |

OTHER PUBLICATIONS

Notification of Transmittal of the International Search Report and the Written Opinion of the International Searching Authority from corresponding PCT/GB2022/051845 dated Oct. 18, 2022.

United Kingdom Search Report from corresponding United Kingdom Application No. 2110380.9 dated Nov. 17, 2021.

United Kingdom Search Report from corresponding United Kingdom Application No. 2110381.7 dated Nov. 17, 2021.

United Kingdom Search and Examination Report from corresponding United Kindgom Application No. 2110381.7 dated Nov. 22, 2024.

U.S. Non-Final Office Action dated Jan. 8, 2026 from corresponding U.S. Appl. No. 18/580,426.

* cited by examiner

ROBOTIC SURGICAL INSTRUMENT

CROSS-REFERENCE TO RELATED APPLICATIONS

This application is a U.S. National Phase Application under 35 U.S.C. § 371 of International Application No. PCT/GB2022/051845, filed Jul. 18, 2022, which claims priority to United Kingdom Application No. 2110380.9, filed Jul. 19, 2021. Each application referenced above is hereby incorporated by reference in its entirety for all purposes.

FIELD OF THE INVENTION

This invention relates to a robotic surgical instrument, in particular to an arrangement for reducing the tilting of a supporting body of the robotic surgical instrument.

BACKGROUND OF THE INVENTION

The field of surgical robotics is rapidly expanding, due to the substantive improvements in precision and sterility that surgical robots offer over manual surgical practices. A typical surgical robot comprises a base unit, a robot arm, and a surgical instrument. The robot arm is connected at a proximal end to the base unit, and at a distal end to the surgical instrument. The surgical instrument, at its distal end, comprises an end effector for penetrating the body of a patient at a port to reach a surgical site where it engages in a medical procedure.

During minimally invasive surgical procedures, a surgical instrument of a surgical robot may be used to hold the tissue or organs of a patient in a set position so that they do not interfere with the surgical operation to be performed. In order to fulfil this function, the tip of the surgical instrument is often required to support heavier loads than those that it is subjected to if it is performing a surgical procedure. If the end effector is a needle holder, then heavy loads may also be experienced by the end effector during suturing operations. During these operations, the patient's tissue exerts a load on the needle which is transmitted to the end effector via the needle holder. A heavy load for a surgical instrument is generally recognised as a load that is greater than 10N.

It is important that the efficiency of the end effector of the surgical instrument is maintained during surgical procedures. This efficiency may be reduced, for example, by obstruction or interference of parts of the surgical instrument with the elements that are used to drive the surgical instrument. A reduction in efficiency of the end effector means that it is less able to perform its intended operation, such as cutting surgical tissue or holding this tissue in place. Obstruction or interference between parts of the surgical instrument may also result in damage to those parts of the instrument, which is detrimental to its performance. This is particularly problematic for instruments with articulated joints, which are structurally weaker and comprise more components than unarticulated instruments. It is also important that unwanted movement or tilting of the components of the surgical instrument is minimised. This unwanted movement can result in a lack of tension in the components used to transfer movement through the surgical instrument, further impacting its performance.

There is a need for an improved arrangement for a robotic surgical instrument that reduces unwanted movement, such as tilting, of the instrument when it is subjected to high loads.

SUMMARY OF THE INVENTION

According to a first aspect, there is provided a robotic surgical instrument comprising: an end effector; a shaft component; a supporting body connected to a distal end of the shaft component at a first end and to the end effector at a second end, the supporting body comprising first and second flanges extending from the first end into the shaft component; a pulley facing an outer surface of the first flange; and a protrusion coupled to the distal end of the shaft component and extending towards the end effector, and configured to interface with an interfacing surface of one of the first or second flanges when the supporting body is moved towards the pulley; wherein the separation between the outer surface of the first flange and the pulley is greater than the separation between said interfacing surface of one of the first or second flanges and the protrusion.

The protrusion may be located between the first and second flanges and said one of the first or second flanges may be the second flange.

The said interfacing surface may be an inner surface of the second flange.

The pulley facing the outer surface of the first flange may be a first pulley and the robotic surgical instrument may further comprise a second pulley facing an outer surface of the second flange, the protrusion being configured to interface with an inner surface of the first flange when the supporting body is moved towards the second pulley. The separation between the outer surface of the second flange and the second pulley may be greater than the separation between the inner surface of the first flange and the protrusion.

When the instrument is in an equilibrium position, the separation between the outer surface of the first flange and the first pulley may be the same as the separation between the outer surface of the second flange and the second pulley.

The separation between the inner surface of the first flange and the inner surface of the second flange may be 0.1 mm greater than the width of the protrusion.

When the instrument is in an equilibrium position, the separation between the inner surface of the first flange and the protrusion may be 0.05 mm.

When the instrument is in an equilibrium position, the separation between the inner surface of the second flange and the protrusion may be 0.05 mm.

The protrusion may be located between the first flange and the pulley, said one of the first or second flanges may be the first flange, and said interfacing surface may be the outer surface of the first flange.

The pulley facing the outer surface of the first flange may be a first pulley and the robotic surgical instrument may further comprise a second pulley facing an outer surface of the second flange. The robotic surgical instrument may further comprise a second protrusion coupled to the distal end of the shaft component and extending towards the end effector. The second protrusion may be located between the second flange and the second pulley and configured to interface with the outer surface of the second flange when the supporting body is moved towards the second pulley. The separation between the outer surface of the second flange and the second pulley may be greater than the separation between said outer surface of the second flange and the protrusion.

The supporting body may be configured to rotate at a first joint about a first axis which is transverse to a longitudinal axis of the shaft component, and the first joint may comprise a pin connected to the supporting body and configured to rotate relative to the shaft component.

The supporting body may comprise a channel extending through its first end and configured to house the pin of the first joint with an interference fit.

The shaft component may further comprise opposing first and second tines that extend distally of the shaft component. The robotic surgical instrument may further comprise a hollow tube rigidly connected to the first end of the supporting body and configured to extend between the first and second tines of the shaft component, the pin of the first joint being configured to pass through the hollow tube such that rotation of the first joint about the first axis results in rotation of the supporting body about the first axis.

The pulley may be configured to rotate at the first joint about the first axis.

The robotic surgical instrument may further comprise a first pair of driving elements configured to drive the first joint of the instrument, the first pair of driving elements comprising a first driving element extending through a first hole in the distal end of the shaft component and a second driving element extending through a second hole in the distal end of the shaft component.

The length of the protrusion may extend along the distal end of the shaft component and along the length of the separation between the first hole and the second hole.

The geometry of the distal end of the protrusion may be complementary to the geometry of the first end of the supporting body.

A distal surface of the protrusion may have a semi-elliptical profile.

A length of the protrusion across the distal end of the shaft component may be between 2.6 mm and 3 mm.

The length of the protrusion may be aligned with an axis running across the middle of the distal end of the shaft component.

The width of each of the first flange and the second flange may be 0.3 mm.

An area of the outer surface of the first flange may be indented at a distal end.

The area of the outer surface of the first flange that is indented may be asymmetrical.

An area of the outer surface of the second flange may be indented at a distal end.

The area of the outer surface of the second flange that is indented may be asymmetrical.

The shaft component may further comprise opposing first and second tines that extend distally of the shaft component, each of the first and second tines comprising an appendage extending distally of its respective tine. Each appendage may be configured to interface with the supporting body when the supporting body is subjected to a force that moves it towards the respective tine of that appendage.

According to a second aspect, there is provided a robotic surgical instrument comprising: an end effector; a shaft component; a first joint extending along a first axis which is transverse to a longitudinal axis of the shaft component; and a supporting body connected to a distal end of the shaft component at a first end and to the end effector at a second end, the supporting body being connected to the distal end of the shaft component by the first joint such that the supporting body is configured to rotate about the first axis, the supporting body comprising a channel extending through its first end and configured to house the pin of the first joint with an interference fit.

According to a third aspect, there is provided a robotic surgical instrument comprising: an end effector; a shaft component comprising opposing first and second tines; a first joint extending along a first axis which is transverse to a longitudinal axis of the shaft component and comprising a pin that is connected to the supporting body and configured to rotate relative to the shaft component; a supporting body connected to a distal end of the shaft component at a first end and to the end effector at a second end, the supporting body being connected to the distal end of the shaft component by the first joint such that the supporting body is configured to rotate about the first axis; and a hollow tube rigidly connected to the first end of the supporting body and configured to extend between the first and second tines of the shaft component, the pin of the first joint being configured to pass through the hollow tube such that rotation of the first joint about the first axis results in rotation of the supporting body about the first axis.

According to a fourth aspect there is provided a robotic surgical instrument comprising: an end effector; a shaft component comprising opposing first and second tines extending distally of the shaft; and a supporting body connected to a distal end of the shaft component at a first end and to the end effector at a second end, the supporting body comprising first and second flanges extending from the first end into the shaft component; wherein each of the first and second tines of the shaft comprises an appendage extending distally of its respective tine, each appendage being configured to interface with the supporting body when the supporting body is subjected to a force that moves it towards the respective tine of that appendage.

BRIEF DESCRIPTION ON THE FIGURES

The present invention will now be described by way of example with reference to the accompanying drawings. In the drawings.

DETAILED DESCRIPTION

Figure 1:
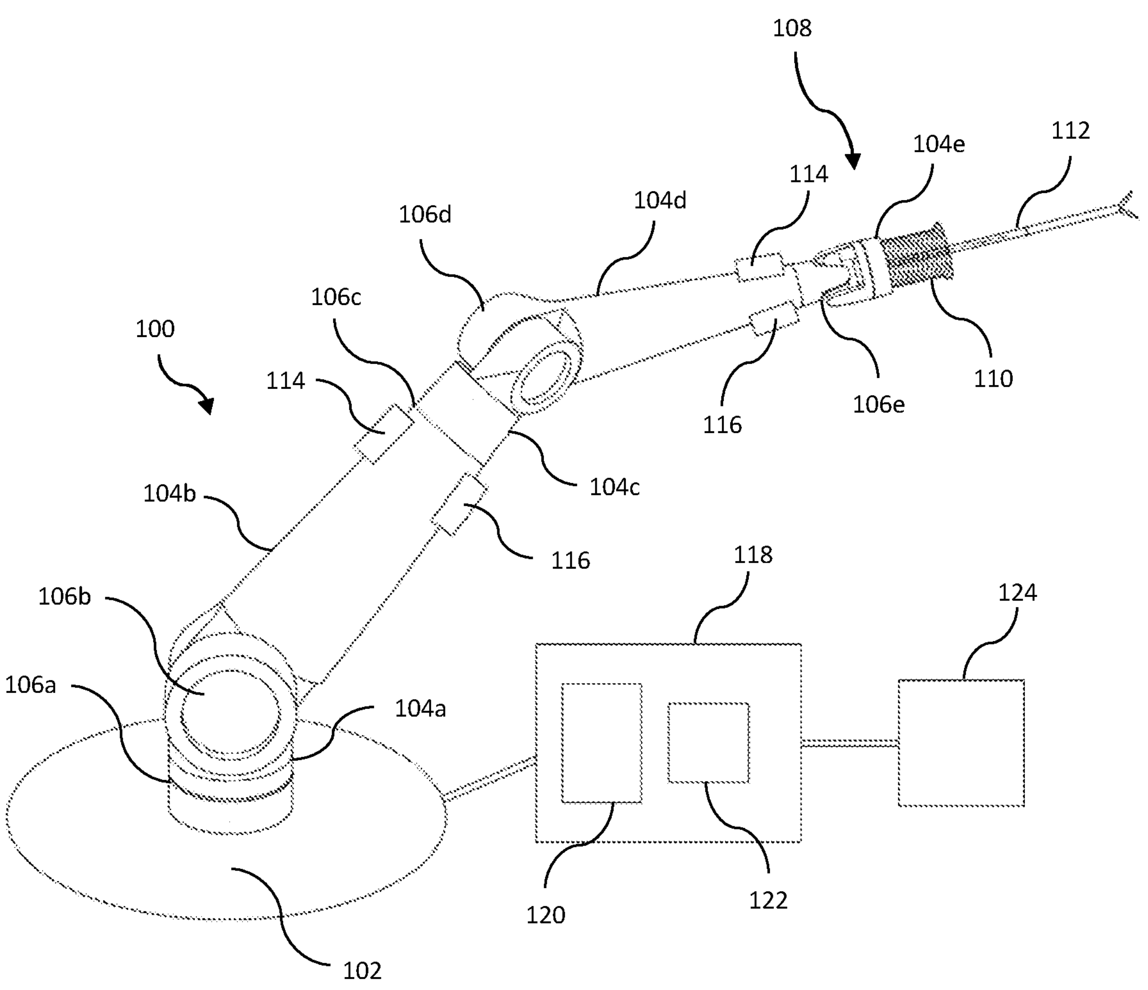
FIG. 1 illustrates a surgical robot.

FIG. 1 illustrates a surgical robot having an arm 100 which extends from a base unit 102. The arm comprises a plurality of rigid limbs 104*a-e* which are coupled by a plurality of joints 106*a-e*. The joints 106*a-e* are configured to apply motion to the limbs. The limb that is closest to the base 102 is the most proximal limb 104*a* and is coupled to the base by a proximal joint 106*a*. The remaining limbs of the arm are each coupled in series by a joint of the plurality of joints 106*b-e*. A wrist 108 may comprise four individual revolute joints. The wrist 108 couples one limb (104*d*) to the most distal limb (104*e*) of the arm. The most distal limb 104*e* carries an attachment 110 for a surgical instrument 112. Each joint 106*a-e* of the arm 100 has one or more drive sources 114 which can be operated to cause rotational motion at the respective joint. Each drive source 114 is connected to its respective joint 106*a-e* by a drivetrain which transfers power from the drive source to the joint. In one example, the drive sources 114 are motors. The drive sources 114 may alternatively be hydraulic actuators, or any other suitable means. Each joint 106*a-e* further comprises one or more configuration and/or force sensors 116 which provides sensory information regarding the current configuration and/or force at that joint. In addition to configuration and/or force sensory data, the one or more sensors 116 may additionally provide information regarding sensed temperature, current or pressure (such as hydraulic pressure).

The arm terminates in an attachment for interfacing with the surgical instrument 112. In examples described herein, the surgical instrument has a diameter less than 8 mm. The surgical instrument may have a 6 mm diameter. The surgical instrument may have a diameter which is less than 6 mm. The surgical instrument comprises an end effector for performing an operation. The end effector may take any suitable form. For example, the end effector may be smooth jaws, serrated jaws, a gripper, a pair of shears, a pair of scissors, a needle for suturing, a camera, a laser, a knife, a stapler, a cauteriser, a suctioner or an electrosurgical instrument such as a pair of monopolar scissors. The surgical instrument further comprises an instrument shaft and an articulation located between the instrument shaft and the end effector. The articulation comprises several joints which permit the end effector to move relative to the shaft of the instrument. The joints in the articulation are actuated by driving elements. These driving elements are secured at the other end of the instrument shaft to interface elements of the instrument interface. The driving elements are elongate elements that extend from the joints in the articulation through the shaft to the instrument interface. Each driving element can be flexed transverse to its longitudinal axis in the specified regions. For example, the driving elements may be cables.

The attachment comprises a drive assembly for driving articulation of the instrument. Movable interface elements of the drive assembly interface mechanically engage corresponding movable interface elements of the instrument interface in order to transfer drive from the robot arm to the instrument. Thus, the robot arm transfers drive to the end effector as follows: movement of a drive assembly interface element moves an instrument interface element which moves a driving element which moves a joint of the articulation which moves the end effector.

Controllers for the drive sources 114 and sensors 116 are distributed within the robot arm 100. The controllers are connected via a communication bus to a control unit 118. The control unit 118 comprises a processor 120 and a memory 122. The memory 122 stores, in a non-transient way, software that is executable by the processor 120 to control the operation of the drive sources 114 to cause the arm 100 to operate. In particular, the software can control the processor 120 to cause the drive sources (for example via distributed controllers) to drive in dependence on inputs from the sensors 116 and from a surgeon command interface 124.

Figure 2:
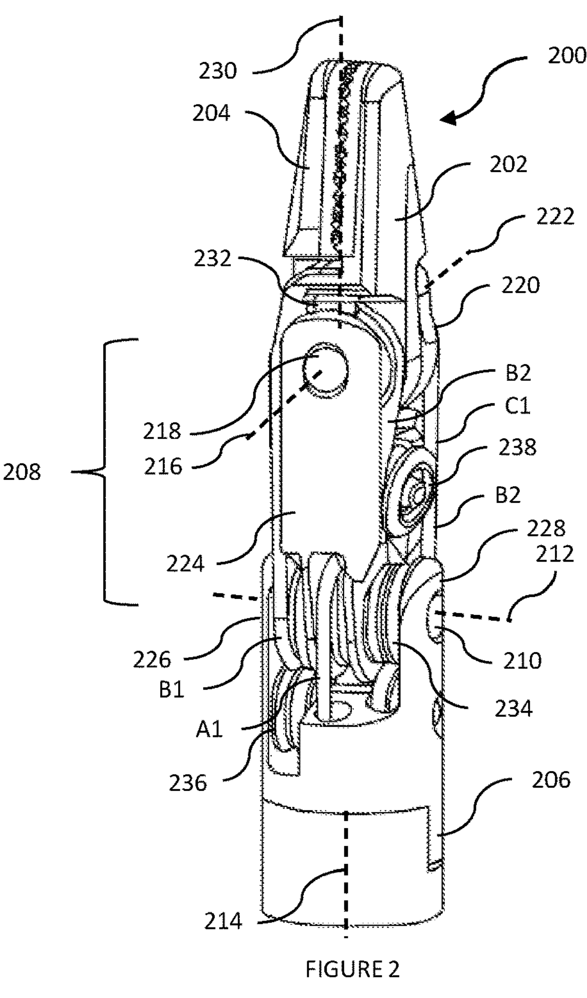
FIG. 2 illustrates a first surgical instrument which could be used with the surgical robot of FIG. 1.

FIG. 2 illustrates a distal end of a surgical instrument for attachment to the arm of a surgical robot. The distal end of the surgical instrument is the end located furthest from the base unit of the surgical robot. The distal end of the surgical instrument comprises an end effector 200 with a pair of opposing end effector elements 202, 204. The end effector 200 is connected to the distal end of the shaft 206 by an articulation 208. The shaft is connected at its proximal end to an interface for attaching to a robot arm. The drive mechanism may comprise a drive source as described with reference to FIG. 1 above.

Articulation 208 comprises joints which permit movement of the end effector 200 relative to the shaft 206. A first joint 210 permits the end effector 200 to rotate about a first axis 212. The first axis 212 is transverse to the longitudinal axis 214 of the shaft. A second joint 218 permits the first end effector element 202 to rotate about the second axis 216. The second axis 216 is transverse to the longitudinal axis of the shaft 214, and to the first axis 212. A third joint 220 permits the second end effector element 204 to rotate about a third axis 222. The third axis 222 is also transverse to the longitudinal axis 214 of the shaft. The third axis 222 may be parallel to the second axis 216. The second and third axes may be the same axis. The first end effector element 202 and the second end effector element 204 may be independently rotatable about the second axis 216 and the third axis 222 respectively by the second and third joints. The end effector elements may be rotated in the same direction or different directions by the second and third joints.

Articulation 208 further comprises a supporting body 224. At a first end, the supporting body 224 is connected to the end effector 200 by the second joint 218 and the third joint 220. At a second end opposing the first end, the supporting body 224 is connected to the shaft 206 by the first joint 210. The second joint 218 and the third joint 220 permit the end effector elements 202, 204 to rotate relative to the supporting body 224 about the second and third axes 216, 222. The first joint 210 permits the supporting body 224 to rotate relative to the shaft 206 about the first axis 212. The distal end of the shaft 206 comprises a first tine 226 and a second tine 228. The first and second tines extend away from the body of the shaft 206 and towards the end effector 200. The first and second tines may extend in a direction that is parallel to the longitudinal axis 214 of the shaft. The first tine 226 of the shaft opposes the second tine 228. That is, the first tine 226 is located on an opposite side of the shaft to the second tine 228. The first tine 226 and the second tine 228 are spaced apart. This enables an arrangement of pulleys and driving elements to be located between the tines. It also enables a first end of the supporting body 224 to be located between the tines.

FIG. 2 illustrates the surgical instrument in a straight configuration. In this configuration, the end effector 200 is aligned with the shaft 206. That is, the longitudinal axis 230 of the end effector is coincident with longitudinal axis 214 of the shaft. The second and third axes 216, 222 are both transverse to the longitudinal axis 214 of the shaft. Articulation of the first, second and third joints enables the end effector to take a range of attitudes relative to the shaft.

Each joint of the end effector is driven by a pair of driving elements. That is, each joint is independently driven. The first joint 210 is driven by a first pair of driving elements A1, A2 (not visible). The second joint 218 is driven by a second pair of driving elements B1, B2. The third joint 220 is driven by a third pair of driving elements C1, C2 (not visible). At one point, driving elements of a pair of driving elements are secured to their corresponding joint. For example, the second pair of driving elements B1, B2 comprises a ball feature 232 which is secured to the second joint 218. The ball feature 232 may be otherwise referred to as a crimp. A pair of driving elements may be constructed as a single piece of material. in this case, the single piece is secured to its respective joint at one point.

The surgical instrument of FIG. 2 further comprises a pulley arrangement around which the first, second and third pairs of driving elements are constrained to move. The pulley arrangement comprises a first set of pulleys 234 rotatable about the first axis 212. That is, the first set of pulleys 234 rotate about the same axis as the first joint 210. The pulley arrangement further comprises at least a second set of pulleys 236 and a pair of redirecting pulleys 238.

Figure 3:
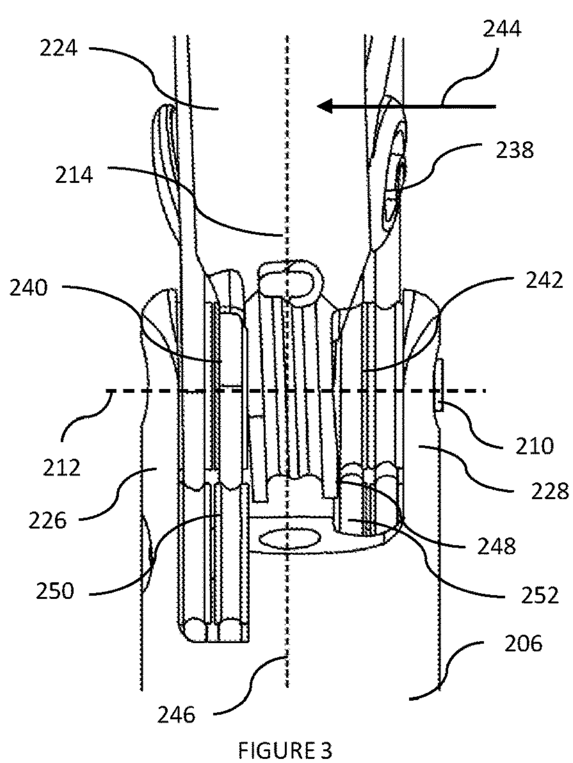
FIG. 3 illustrates a portion of the surgical instrument illustrated in FIG. 2 in a situation in which it experiences a problem.

The first set of pulleys further comprises a first pulley 240 and a second pulley 242, which are visible from FIG. 3. Both the first pulley 240 and the second pulley 242 rotate about the first axis 212. The first pulley 240 and the second pulley 242 of the first set of pulleys are located on opposing sides of the first joint 210 along the longitudinal axis 214 of the shaft. The first pulley 240 and the second pulley 242 are located on opposing sides of the first pair of driving elements A1, A2. The first pair of driving elements A1, A2 are routed around the proximal end of the supporting body so that they enable rotation of the supporting body about the first joint 210. The proximal end of the supporting body is the end of the supporting body that is closest to the shaft. The first pulley 240 is located between the supporting body 224 and the first tine 226 of the shaft. The second pulley 242 is located between the supporting body 224 and the second tine 228 of the shaft.

Correspondingly, the second set of pulleys further comprises a first pulley 250 and a second pulley 252. The first pulley 250 and the second pulley 252 of the second set of pulleys are located on opposing sides of the shaft. The first pulley 250 and the second pulley 252 are located on opposing sides of the first pair of driving elements A1, A2. The first pulley 250 of the second set of pulleys is located between the supporting body 224 and the first tine 226 of the shaft. The second pulley 252 of the second set of pulleys is located between the supporting body 224 and the second tine 228 of the shaft.

A problem with the arrangement of a surgical instrument as illustrated in FIG. 2 is illustrated in FIG. 3. Note that driving element A1 of the surgical instrument is omitted from FIG. 3 for clarity.

During a surgical procedure, the distal end of the surgical instrument is subjected to external forces that act to push the end effector element and supporting body in an unintended direction. That is, the external forces act to disrupt the position of the end effector element and the supporting body from their equilibrium position. In an equilibrium position, the longitudinal axis of the end effector and the supporting body are aligned with the longitudinal axis of the shaft along a common axis 246. The external forces may arise from the end effector element interacting with a part of patient, or the surgical site, or with an item of surgical equipment. The external forces may cause the end effector and the supporting body of the surgical instrument to move (e.g., tilt or rotate) relative to the shaft. In FIG. 3 the supporting body is subjected to a force in a direction 244 that pushes the end effector element and supporting body towards the first tine 226 of the shaft 206. It would be understood that the force may alternatively act in an opposing direction and push the end effector element towards the second tine 228 of the shaft 206. The force may otherwise act in any other direction at any given angle with respect to the common axis 246.

There is a degree of clearance between the components that rotate about the first joint 210 of the surgical instrument. This clearance may vary for different surgical instruments, as it is dependent on the mechanical tolerances required by the instrument. The components that rotate about the first joint are the first pair of driving elements A1, A2, the supporting body 224, the first pulley 240 and the second pulley 242. The clearance between these components allows the supporting body to tilt about an axis of tilt that is perpendicular to the first axis 212 and to the common axis 246 shared by the shaft, the supporting body and the end effector when they are aligned. The clearance also allows the supporting body to be displaced linearly along the first axis 212. As the supporting body 224 moves about the axis of tilt or along the first axis 212 as guided by the external force, a distal end of the supporting body begins to interfere with a pulley of the surgical instrument at a location 248. In one example, as illustrated in FIG. 3, this pulley is the second pulley 252 of the second set of pulleys 236. In this example the supporting body 224 interferes with the second pulley 252 of the second set of pulleys 236 at an upper edge of the second pulley. The supporting body may additionally or alternatively interfere with the first pulley 240 of the first set of pulleys 234 at an upper edge of the first pulley 240. This interference impedes the rotation of the respective pulley and reduces the efficiency of the driving elements that are directed around that pulley. This ultimately reduces the efficiency of the parts of the end effector that are driven by the driving elements. The same is true of the first pulley 250 of the second set of pulleys 236, the second pulley 242 of the first set of pulleys 234, and their respective driving elements if the external force acts in an opposing direction to the direction 244.

The movement (e.g., tilting) of the supporting body 224 in direction 244 (or an alternative direction) may also cause the supporting body to bend, which could result in the permanent deflection of this component. Thus, allowing substantive tilting of the supporting body can result in damage to the surgical instrument, further decreasing its efficiency. It is therefore important to reduce the tilting motion of the supporting body resulting from external forces that are applied to the end effector and/or the supporting body.

Figure 4:
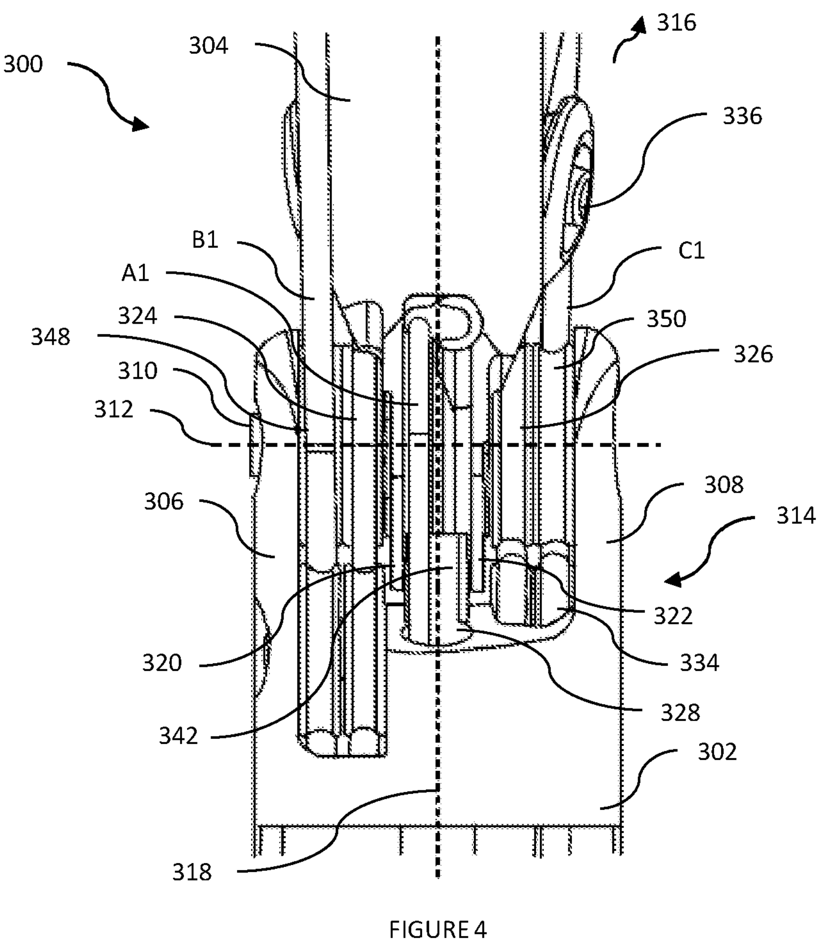
FIG. 4 illustrates a portion of an embodiment of a surgical instrument to be used with the surgical robot of FIG. 1.

FIG. 4 illustrates a portion of an embodiment of a surgical instrument 300 to be used with the surgical robot of FIG. 1. More specifically, FIG. 4 illustrates the proximal end of the surgical instrument. Some aspects of the embodiment of the surgical instrument shown in FIG. 4 are the same as those of the instrument illustrated in FIG. 2. That is, the surgical instrument of FIG. 4 comprises a shaft 302 and a supporting body 304. The supporting body is connected to the distal end of the shaft. The distal end of the shaft is the end furthest from the robot arm. The shaft 302 comprises a first tine 306 and a second tine 308. The first and second tines extend away from the body of the shaft 302. That is, the first and second tines extend distally of the shaft 302. The first and second tines may extend in a direction that is parallel to the longitudinal axis 318 of the shaft. The first tine 306 of the shaft 302 opposes the second tine 308. That is, the first tine 306 is located on an opposite side of the shaft 302 to the second tine 308. The first tine 306 and the second tine 308 are spaced apart. This enables an arrangement of pulleys and driving elements to be located between the tines. It also enables a first end of the supporting body to be located between the tines.

In an example, the shaft 302 may comprise one or more separate components, where a distal shaft component interfaces with the end effector. The distal shaft component may be separate to the rest of the shaft, which may otherwise referred to as the body of the shaft. References to a “shaft” should be understood as referring to a shaft “component”, where the term “component” refers to either the shaft as a whole or a separate, distal component that forms part of the shaft and is attached to the body of the shaft. Where the shaft component is a separate component to the body of the shaft, the shaft component may be moveably attached to the body of the shaft by one or more driving elements that allow the shaft component to be tensioned and relaxed with respect to the body of the shaft. The one or more driving elements may be cables. Alternatively, the separate shaft component may be a component that is rigidly attached to the body of the shaft, for example using an adhesive or by spot welding.

The supporting body 304 is connected to the shaft 302 at a first end 314. In other words, the first end 314 of the supporting body is the end that is closest to the shaft 302. The supporting body 304 is connected to the end effector at a second end 316. In other words, the second end 316 of the supporting body is the end that is closest to the end effector. The second end 316 may oppose the first end 314 of the supporting body.

The surgical instrument 300 comprises a first joint 310 which permits the end effector to rotate about a first axis 312. More specifically, the supporting body 304 is configured to rotate about the first joint 310. The first joint comprises a pin that is connected to the supporting body 304. The pin is configured to rotate relative to the shaft 302, thereby rotating the supporting body 304 relative to the shaft 302. As the end effector is connected to the second end 316 of the supporting body, rotation of the supporting body about the first joint 310 enables rotation of the end effector about the first joint. The first axis 312 is transverse to the longitudinal axis 318 of the shaft.

The arrangement of pulleys of the surgical instrument 300 comprises a first set of pulleys which are rotatable about the first joint 310. The first set of pulleys comprises a first pulley 324 and a second pulley 326. The first and second pulleys 324, 326 may correspond to first and second pulleys 240, 242 illustrated in FIG. 3. Both the first pulley 324 and the second pulley 326 rotate about the first axis 312. The first pulley 324 and the second pulley 326 are located on opposing sides of the first joint 210 along the longitudinal axis 318 of the shaft. The first pulley 324 and the second pulley 326 are located on opposing sides of the first pair of driving elements A1, A2. The first pair of driving elements A1, A2 are routed around a feature located at the proximal end of the supporting body so that they enable rotation of the supporting body about the first joint 310. The proximal end of the supporting body is the end of the supporting body that is closest to the shaft 302. The first pulley 324 is located between the supporting body 304 and the first tine 306 of the shaft. The second pulley 326 is located between the supporting body 304 and the second tine 308 of the shaft.

In some examples, the first set of pulleys may further comprise a third pulley 348 and a fourth pulley 350. The second set of pulleys may also comprise a corresponding third pulley and a corresponding fourth pulley. The first and second pulleys of the first and second sets of pulleys may be configured to route a first driving element B1, C1 of the first and second sets of driving elements around them. The third and fourth pulleys of the first and second sets of pulleys may be configured to route a second driving element B2, C2 of the second and third pairs of driving elements around them.

The distal end of the surgical instrument 300 of FIG. 4 may be the same as the distal end of the surgical instrument illustrated in FIG. 2. That is, the end effector may comprise a pair of opposing end effector elements as illustrated in FIG. 2. The end effector may be rotatable about first and second joints corresponding to the joints 218, 220 illustrated in FIG. 2. Alternatively, the end effector may take any other suitable form such as a gripper, a pair of shears, a pair of scissors, a needle for suturing, a camera, a laser, a knife, a stapler, a cauteriser, a suctioner or an electrosurgical instrument such as a pair of monopolar scissors.

Figure 5:
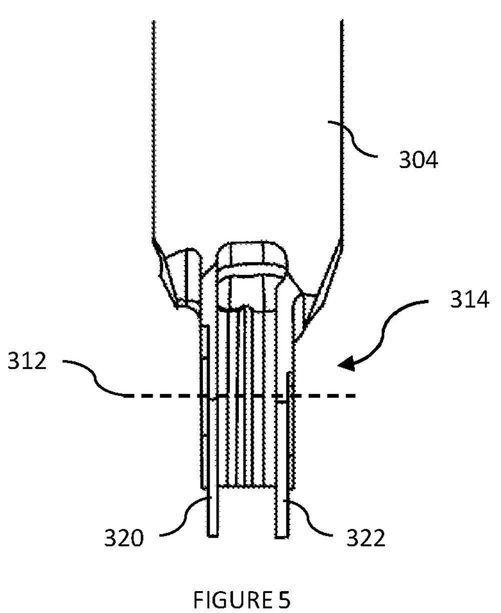
FIG. 5 illustrates the configuration of the supporting body used in the embodiment of the surgical instrument of FIG. 4.

The supporting body 304 comprises a first flange 320 and a second flange 322. The first and second flanges are protrusions of material that extend away from the centre of the supporting body. That is, the first and second flanges extend distally from the centre of the supporting body. The first end 314 of the supporting body is located between the tines 306, 308 of the shaft 302. Thus, the first and second flanges 320, 322 of the supporting body are located within the shaft and extend distally into the shaft. That is, the first and second flanges 320, 322 extend towards the body of the shaft 302. In other words, the first and second flanges 320 extend from the supporting body into the shaft in a direction aligned with the longitudinal axis of the supporting body. The first flange 320 and the second flange 322 are located on opposing sides of the first end 314 of the supporting body. The first flange 320 and the second flange 322 are located on opposing sides of the first pair of driving elements A1, A2. The first flange 320 and the second flange 322 are illustrated more clearly in FIG. 5, which illustrates the first end 314 of the supporting body 304 in isolation. It can be seen from FIG. 5 that the first end of the supporting body is narrower than the centre of the supporting body. This is so that the first end of the supporting body can be located between the first pulley 324 and the second pulley 326, and within a space defined by the first tine 306 and the second tine 308 of the shaft 302.

The first and second flanges have two purposes. The first purpose is to provide a guide for the first pair of driving elements A1, A2 that are routed around the first end 314 of the supporting body. The second purpose is described in further detail below. The first and second flanges may each have a width of between 0.1 and 0.5 mm. This ensures that the flanges are thin enough to be located between the tines of the shaft 302 but thick enough to withstand the operative forces that they are subjected to without breaking. In a specific, optimised, example the first and second flanges may each have a width of 0.3 mm.

The first joint 310 is driven by a first pair of driving elements A1, A2 (not visible). The first pair of driving elements A1, A2 are routed around the first end 314 of the supporting body so that they enable rotation of the supporting body about the first joint 310. In other words, the first pair of driving elements are configured to drive the first joint 310 of the surgical instrument. The first joint 310 may be driven by a further pair of driving elements in addition to the first pair of driving elements. In FIG. 4, only the first driving element of a first pair of driving elements is illustrated. A further pair of driving elements may also be routed around the first end 314 of the supporting body, in addition to the first pair of driving elements, so that they enable rotation of the supporting body about the first joint 310. The first driving element A1 of the first pair of driving elements extends out of the distal end of the shaft 302 from a first hole 328 located in the distal end of the shaft. The second driving element A2 (not visible) of the first pair of driving elements extends out of the distal end of the shaft 302 from a second hole 330. The second hole 330 is visible in FIG. 6, which illustrates a second side of the distal end of the shaft 302 in isolation. The second side of the distal end of the shaft is symmetrical to the first side of the shaft. That is, the second side of the distal end of the shaft, relative to a first plane 332, is symmetrical to the first side of the distal end of the shaft relative to this plane. The first plane intersects the first tine 306 and the second tine 308, and is parallel to the longitudinal axis 318 of the shaft.

The surgical instrument may further comprise second and third joints that are driven by second and third pairs of driving elements. These joints and their driving elements correspond to joints 218 and 220, second pair of driving elements B1, B2 and third pairs of driving elements C1, C2 as illustrated in FIG. 2. Second and third pairs of driving elements may drive other joints in a similar way to that which is illustrated in FIG. 2. The pulley arrangement further comprises at least a second set of pulleys 334 and a pair of redirecting pulleys 336, which correspond to those illustrated in FIG. 2. The second set of pulleys 334 is located proximally of the first set of pulleys. That is, the second set of pulleys 334 is located closer to the robot arm and further from the supporting body 304 than the first set of pulleys.

The first pulley 324 of the surgical instrument illustrated in FIG. 4 faces an outer surface of the first flange 320. The outer surface of the first flange 320 is the surface of the first flange that faces the first tine 306 of the shaft 302. The outer surface of the first flange is on an opposing side of the flange to an inner surface of the first flange. The inner surface of the first flange 320 is the surface of the second flange 322 that faces the first pair of driving elements A1, A2. The second pulley 326 of the surgical instrument faces an outer surface of the second flange 322. The outer surface of the second flange 322 is the surface of the second flange 322 that faces the second tine 308 of the shaft 302. The outer surface of the second flange 322 is on an opposing side of the flange to an inner surface of the second flange. The inner surface of the second flange 322 is the surface of the second flange 322 that faces the first pair of driving elements A1, A2.

The surgical instrument further comprises a protrusion 342 coupled to (i.e. fixed to) the distal end of the shaft 302. The protrusion 342 extends from the distal end of the shaft 302 towards the end effector that is coupled to the second end 316 of the supporting body 304. The protrusion 342 is located between the first flange 320 and the second flange 322. An enlarged view of the surgical instrument at the first end 314 of the supporting body can be seen in FIG. 7. From this enlarged view it can be seen that the protrusion 342 is separated from the first flange 320 by a first distance, or separation, d1. The protrusion faces the inner surface of the first flange, so the separation d1 is between the inner surface of the first flange 320 and the protrusion 342. Similarly, the protrusion 342 is separated from the second flange 322 by a second distance, or separation, d2. The protrusion faces the inner surface of the second flange, so the separation d2 is between the inner surface of the second flange 322 and the protrusion 342. d1 is a non-zero distance. d2 is a non-zero distance.

The first flange 320 is separated from the first pulley 324 by a third distance, or separation, d3. The first pulley 324 faces the outer surface of the first flange, so the separation d3 is between the outer surface of the first flange 320 and the first pulley 324. Similarly, the second flange 322 is separated from the second pulley 326 by a fourth distance, or separation, d4. The second pulley 326 faces the outer surface of the second flange 322, so the separation d4 is between the outer surface of the second flange 322 and the second pulley 326. d3 is a non-zero distance. d4 is a non-zero distance.

The first and second separations d1, d2 are smaller than the third and fourth separation separations d3, d4. In other words, the separation between the inner surface of the first flange 320 and the protrusion 342 is smaller than the separation between the outer surface of the first flange 320 and the first pulley 324. The separation between the inner surface of the first flange 320 and the protrusion 342 is smaller than the separation between the outer surface of the second flange 322 and the second pulley 326. The separation between the inner surface of the second flange 322 and the protrusion 342 is smaller than the separation between the outer surface of the second flange 322 and the second pulley 326. The separation between the inner surface of the second flange 322 and the protrusion 342 is smaller than the separation between the outer surface of the first flange 320 and the first pulley 324. Put differently, the separation between the outer surface of the first flange 320 and the first pulley 324 is greater than the separation between the inner surface of the second flange 322 and the protrusion 342. The separation between the outer surface of the second flange 322 and the second pulley 326 is greater than the separation between the inner surface of the first flange 320 and the protrusion 342.

The protrusion 342 is positioned between the first flange 320 and the second flange 322 in such a way that, when the supporting body 304 is moved (e.g., rotated) towards the first pulley 324, the protrusion 342 is configured to interface with the inner surface of the second flange 322. That is, when the supporting body 304 is moved (e.g., rotated) towards the first pulley 324 in a first direction 338 (illustrated in FIG. 7), the supporting body will move (e.g., tilt) so that at least part of the inner surface of the second flange 322 interferes (i.e., interfaces) with the protrusion, e.g., with a distal end 344 of the protrusion. The distal end 344 of the protrusion is the end of the protrusion that is furthest from the body of the shaft 302. As the separation d2 between the second flange 322 and the protrusion 342 is smaller than the separation d3 between the first flange 320 and the first pulley 324, movement (e.g., rotation) of the supporting body 304 will be limited by interaction between the second flange 322 and the protrusion 342 before the first flange 320 is able to interact with the first pulley 324.

Similarly, when the supporting body is moved (e.g., rotated) towards the second pulley 326, the protrusion 342 is configured to interface with the inner surface of the first flange 324. That is, when the supporting body 304 is moved (e.g., rotated) towards the second pulley 326 in a second direction 340 (illustrated in FIG. 7), the supporting body will move (e.g., tilt) so that at least part of the inner surface of the first flange 320 interferes (i.e., interfaces) with the protrusion, e.g., with a distal end of the protrusion 342. As the separation d1 between the first flange 324 and the protrusion 342 is smaller than the separation d4 between the second flange 322 and the second pulley 326, rotation or axial movement of the supporting body 304 will be limited by interaction between the first flange 320 and the protrusion 342 before the second flange 322 is able to interact with the second pulley 326.

The arrangement of a surgical instrument described with respect to FIGS. 4-7 is advantageous as the protrusion 342 acts to limit the movement (e.g., the tilting) of the supporting body 304 when it is subjected to external forces. As separation d1 is smaller than separation d4, interference between the protrusion 342 and first flange 320 will prevent the second flange 322 from coming into contact with the second pulley 326 when the supporting body is moved (e.g., tilted) in the second direction 340. This means that the driving elements that are driven around the second pulleys of the first and/or second sets of pulleys will not be obstructed by the supporting body 304 and the efficiency of the end effector element that is driven by these driving elements can be maintained. Similarly, as separation d2 is smaller than separation d3, interference between the protrusion 342 and second flange 322 will prevent the first flange 320 from coming into contact with the first pulley 324 when the supporting body is moved (e.g., tilted) in the first direction 338. This means that the driving elements that are driven around the first pulleys of the first and/or second sets of pulleys will not be obstructed by the supporting body 304 and the efficiency of the end effector element that is driven by these driving elements can be maintained. In other words, the protrusion 342 improves the structural rigidity to the surgical instrument.

The protrusion 342 may be located and/or shaped so that it does not interact with the first and second pulleys 324, 326 that rotate about the first axis. Firstly, the protrusion 342 may be located proximally of the first and second pulleys 324, 326 so that it does not interfere with the pulleys. Secondly, the protrusion 342 is located between the flanges of the supporting body, and has a width that is less than the distance between the flanges of the supporting body. By not interfering with the pulleys 324, 326, the protrusion 342 does not take up any additional space along the diameter of the shaft between the flanges and the pulleys that rotate about the first axis 312. This means that the function of the protrusion can be fulfilled without increasing the overall diameter of the instrument to accommodate additional space for the protrusion between the supporting body and the first and second pulleys.

Figure 7:
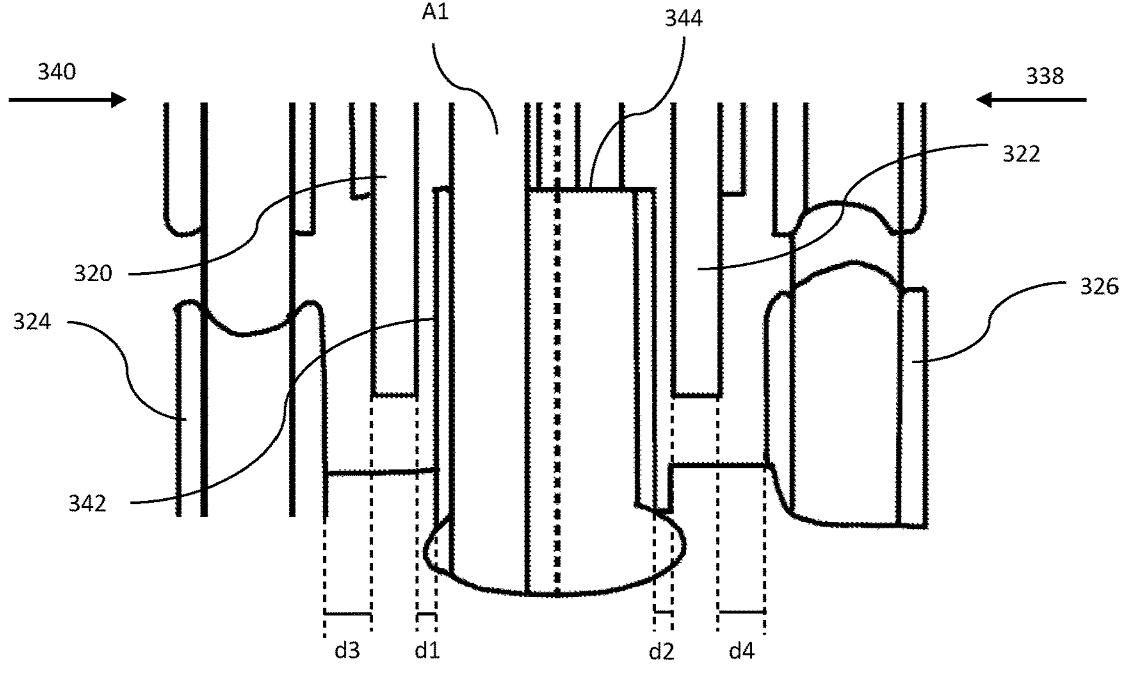
FIG. 7 illustrates an enlarged view of part of the embodiment of the surgical instrument of FIG. 4 at the first end of the supporting body.

The surgical instrument illustrated in FIGS. 4 and 7 comprises a first set of pulleys comprising a first pulley and a second pulley. In an alternative example, the first set of pulleys may comprise only a single pulley. In this example, the single pulley may face the outer surface of the first flange the protrusion may be configured to interface with an inner surface of the second flange when the supporting body is rotated towards that pulley.

When the instrument is in an equilibrium position (i.e., a neutral position), e.g., when there are no external forces on the instrument, the separation between the outer surface of the first flange 320 and the first pulley 324 may be the same as the separation between the outer surface of the second flange 322 and the second pulley 326. That is, the separation d3 may be equal to separation d4. As the surgical instrument may be subjected to external forces in a first direction 338 of equal magnitude to the forces that it is subjected to in a second direction 340, it is advantageous that the tilting motion of the supporting body is equally limited in both directions. The separations d3 and d4 should be non-zero values. The separations d1 and d2 may also be non-zero values. By ensuring that all of the separation values d1-d4 are non-zero, it is ensured that the supporting body 304 and pulleys 324, 326 have sufficient clearance to enable their rotation about the first joint 310.

Figure 6:
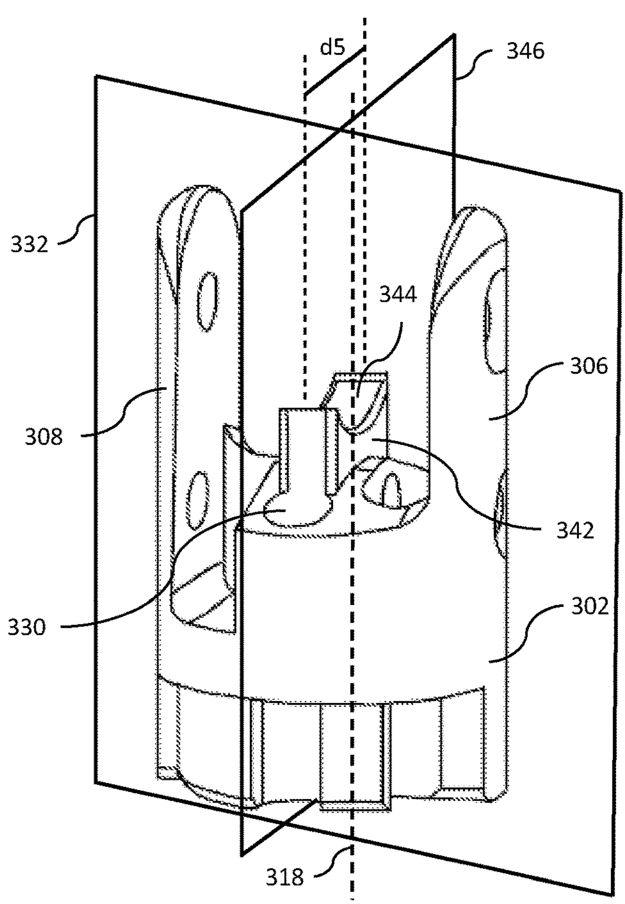
FIG. 6 illustrates the configuration of the distal end of the shaft used in the embodiment of the surgical instrument of FIG. 4.

The geometry of the distal end of the protrusion 342 may be complementary to the geometry of the first end 314 of the supporting body 304. That is, the geometry of the distal end of the protrusion may have a profile that follows the profile of the second end of the supporting body 304. This would ensure that rotation of the supporting body 304 about the first joint 310, relative to the shaft 302, is smooth and unconstrained. That is, by ensuring that the geometry of the protrusion is complementary to the geometry of the supporting body, unwanted interference between the supporting body and the protrusion can be reduced. As an example, the first end 314 of the supporting body may terminate in a surface that has a convex profile. The distal end of the protrusion 342 may terminate in a surface that is concave and that follows the profile of the first end of the supporting body. The surface at which the first end of the supporting body terminates may be semi-elliptical (e.g., semi-circular) in profile. The distal surface of the protrusion may also have a semi-elliptical (e.g., semi-circular) profile 344, as illustrated in FIG. 6. A semi-elliptical profile, in particular a semi-circular profile, for both the terminating surface of the supporting body and the distal end of the protrusion is advantageous as it allows the rotation of the supporting body 304 about the first axis 312 to be guided by the protrusion 342. A semi-elliptical profile also allows the height of the protrusion to be maximised. The height of the protrusion is the dimension of the protrusion that extends in a direction parallel to the longitudinal axis 318 of the shaft. Maximising the height of the protrusion allows the protrusion to provide a maximum level of support to the supporting body whilst ensuring that the intended rotation of the supporting body about the first joint is not limited.

The outer surfaces of the protrusion and the inner surfaces of the proximal end of the supporting body may be designed so that there is minimal friction between these two components as they come into contact and slide or rotate relative to each other. This can be achieved by minimising the contact area between these two components by having a low friction coating or surface finish. Alternatively, or additionally, the surface of the protrusion could be curved instead of flat. This modification would also minimise the contact area between the supporting body and the protrusion.

To give some examples of suitable dimensions, the separation between the inner surface of the first flange 320 and the inner surface of the second flange 322 may be 0.1 mm greater than the width of the protrusion 342. That is, the sum of separation d1 and separation d2 may be 0.1 mm. This value provides sufficient clearance for the supporting body 304 and driving elements A1, A2 to rotate about the first joint 310, whilst also ensuring that interference between the protrusion and either the first or second flange prevents interference of the supporting body with the second or first pulley, respectively. When the instrument is in the equilibrium position, the separation d1 may be equal to the separation d2. Where the sum of d1 and d2 is 0.1 mm, the separation d1 may be 0.05 mm. In other words, the separation between the inner surface of the first flange 320 and the protrusion 342 may be 0.05 mm. The separation d2 may also be 0.05 mm. In other words, the separation between the inner surface of the second flange 322 and the protrusion 342 may be 0.05 mm. By ensuring that the values of separation d1 and separation d2 are the same, as described above with respect to d3 and d4, it is advantageous that the tilting motion of the supporting body is equally limited in both a first direction 338 and a second, opposing direction 340.

As mentioned above, the first and second driving elements A1, A2 extend out of the distal end of the shaft 302 from first and second holes 328, 330 respectively. The length d5 of the protrusion 342 may be so that it extends across the distal end of the shaft along the length of the separation between the first hole 328 and the second hole 330. Constraining the length d5 of the protrusion 342 in this way means that the surface area that can interfere with the first and second flanges is maximised, whilst also ensuring that the protrusion 342 does not interfere with the movement of the driving elements A1, A2 about the first joint. The length of the protrusion may be between 2.6 mm and 3 mm. In a more specific example, the length of the protrusion may be 2.8 mm. The surgical instrument as a whole, including the shaft, may have a 6 mm diameter or a diameter of less than 6 mm. By limiting the length d5 of protrusion within this preferred range of values, the guidance offered to the supporting body 304 by the protrusion 342 can be maximised whilst ensuring that the protrusion, and if necessary holes 328, 330 for the driving elements A1, A2, can be located within the distal end of the shaft.

The length of the protrusion may be aligned with a second plane 346 running across the middle of the distal end of the shaft. The second plane 346 is perpendicular to the first plane 332 and parallel to the longitudinal axis 318 of the shaft. In other words, the protrusion is centrally aligned with respect to the distal end of the shaft. This central alignment assists the central positioning of the supporting body 304 with respect to the shaft 302.

Figure 8:
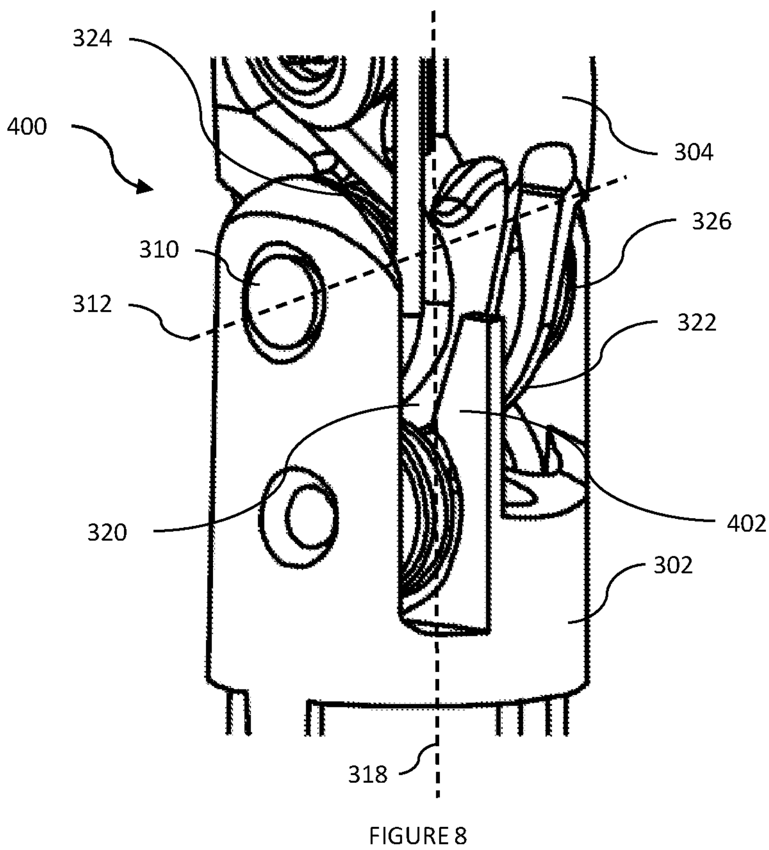
FIG. 8 illustrates a second configuration of a surgical instrument to be used with the surgical robot of FIG. 1.

An alternative example of a surgical instrument 400 for use with a surgical robot as illustrated in FIG. 1 is shown in FIG. 8. The surgical instrument 400 is substantially the same as the surgical instrument 300 illustrated in FIG. 4. The supporting body 304 of the instrument 400 is the same as the supporting body of the surgical instrument 300 of FIG. 4. The pulley arrangement of the surgical instrument 400 is also the same as the corresponding arrangement of the instrument 300 illustrated in FIG. 4. As with the surgical instrument of FIG. 4, the surgical instrument of FIG. 8 comprises a first protrusion 402 coupled to the distal end of the shaft 302. The first protrusion 402 extends towards an end effector that is attached to the supporting body 304.

A distinction between the surgical instrument 400 of FIG. 8 and the corresponding instrument 300 of FIG. 4 is that the first protrusion 402 is located between the outer surface of the first flange 320 of the supporting body and the first pulley 324 of the first set of pulleys. In contrast, the protrusion 342 of FIG. 4 is located between the first and second flanges 320, 322 of the supporting body 304. The first protrusion 402 of surgical instrument 400 is configured to interface with the first flange 320 of the supporting body 304 when the supporting body is moved towards the first pulley 324.

The surgical instrument illustrated in FIG. 8 may also include a second protrusion (not illustrated). The second protrusion may also be coupled to the distal end of the shaft 302 and may extend towards an end effector that is attached to the supporting body 304. The second protrusion may be located between the second flange 322 of the supporting body and the second pulley 326 of the first set of pulleys. Thus, the second protrusion may be configured to interface with the outer surface of the second flange 322 when the supporting body 304 is moved towards the second pulley 326. The first and second protrusions may be arranged symmetrically along the distal end of the shaft 302 with respect to a plane that corresponds to plane 346 illustrated in FIG. 6. That is, the plane about which the first and second protrusions may be symmetrical is parallel to the longitudinal axis 318 of the shaft and perpendicular to the first axis 312 about which the end effector is permitted to rotate.

The separation between the outer surface of the first flange 320 and the first pulley 324 of the surgical instrument 400 is greater than the separation between the outer surface of the first flange and the protrusion 402. This is self-explanatory, as the first protrusion 402 is located between the first flange 320 and the first pulley 324. The same is true of a second protrusion located between the second flange and the second pulley. That is, the separation between the outer surface of the second flange 322 and the second pulley 326 is greater than the separation between the outer surface of the second flange 322 and the second protrusion.

As with the protrusion 342 of FIG. 4, the lengths of the first and second protrusions of surgical instrument 400 may be between 2.6 mm and 3 mm. In a more specific example, the length of the protrusion may be 2.8 mm.

The one or more protrusions of the exemplary arrangement illustrated in FIG. 8 perform the same function as those that are illustrated in FIG. 4. That is, the protrusions 402 act to limit the movement (e.g., the tilting) of the supporting body 304 when it is subjected to external forces. As separation between the first protrusion 402 and the first flange 320, for example, is smaller than separation between the first flange 320 and the first pulley 324, interference between the first protrusion and first flange prevents the first flange from coming into contact with the first pulley when the supporting body 304 is moved (e.g., tilted) towards the first pulley. This means that the driving elements that are driven around the first pulleys of the first and/or second sets of pulleys will not be obstructed by the supporting body 304 and the efficiency of the end effector element that is driven by these driving elements can be maintained.

Similarly, as the separation between the second protrusion and the second flange 322 is smaller than separation between the second flange 322 and the second pulley 326, interference between the second protrusion and second flange prevents the second flange from coming into contact with the second pulley when the supporting body 304 is moved (e.g., tilted) towards the second pulley. This means that the driving elements that are driven around the second pulleys of the first and/or second sets of pulleys will not be obstructed by the supporting body 304 and the efficiency of the end effector element that is driven by these driving elements can be maintained.

The height of the first and second protrusions may be such that they do not extend distally beyond the first axis 312 of the instrument. Preferably, the first and second protrusions are located and/or shaped so that they do not interact with the first and second pulleys 324, 326 that rotate about the first axis. The protrusions may be located proximally of the first and second pulleys 324, 326 so that they do not interfere with the pulleys. As illustrated in FIG. 8, the protrusions may be located forward (i.e. to the right of the first axis 312 as illustrated in FIG. 8) of the first and second pulleys 324, 326 so that they do not interfere with the pulleys. The protrusions may alternatively be located backward (i.e., to the left of the first axis 312 as illustrated in FIG. 8) of the first and second pulleys 324, 326 so that they do not interfere with the pulleys. The protrusions may be shaped so that they extend forward and backward of the first and second pulleys 324, 326, but so that their height is decreased around the pulleys so that they do not interfere with the pulleys. By not interfering with the pulleys 324, 326, the first and second protrusions do not take up any additional space along the diameter of the supporting body between the flanges and the pulleys that rotate about the first axis 312. This means that the function of the protrusions can be fulfilled without increasing the overall diameter of the instrument to accommodate additional space for the first and second protrusions between the supporting body and the first and second pulleys.

Figure 9:
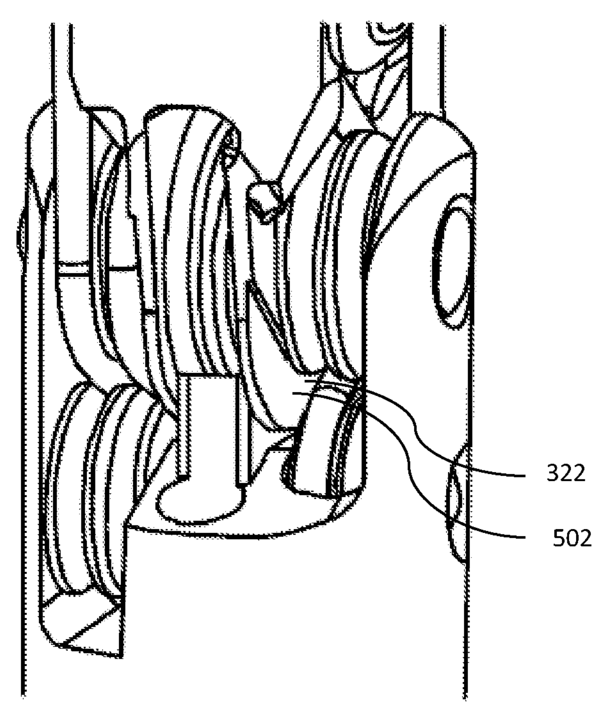
FIG. 9 illustrates a portion of the surgical instrument in a modified example.

In a modified example of the robotic surgical instruments illustrated in either FIG. 4 or FIG. 8, which is shown in FIG. 9, the outer surfaces of the first and second flanges may be modified so that an area at the distal ends of these surfaces is indented. In other words, the first and second flanges may be modified to remove some material from the distal ends of their outer surfaces. This removal of material is indicated in FIG. 9, in which the outer surface of the second flange 322 is indented at its distal end 502. The first flange 320 may be modified similarly.

The removal of material from the outer surfaces of the first and second flanges is provided to reduce interference between the flanges and other components of the surgical instrument. For example, as mentioned above, the surgical instrument comprises a second set of pulleys 334 that is located proximally of the first set of pulleys. In addition to the first set of pulleys, it may be important that tilting of the supporting body 304 does not result in interference between the supporting body and the second set of pulleys 334. This interference could result in a similar loss of efficiency of the end effector to that which results from interference between the supporting body and the pulleys of the first set of pulleys. Removing material from the portion of the outer surfaces of the flanges that is adjacent to the first pulleys reduces the likelihood of this interference.

Figure 10:
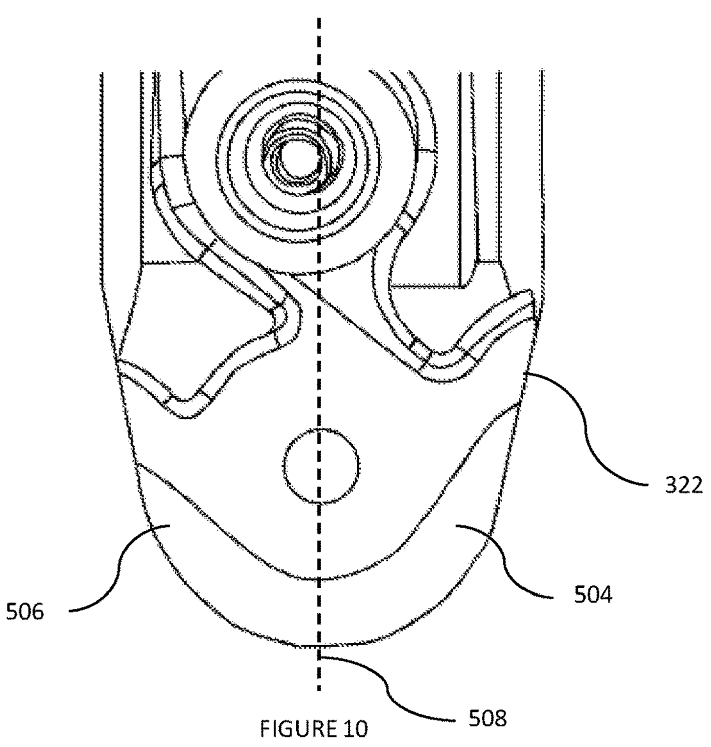
FIG. 10 illustrates a view of the supporting body for the modified surgical instrument of FIG. 9.

FIG. 10 illustrates a view of the second flange of the modified supporting body in the surgical instrument of FIG. 9. From this figure, it can be seen that the area of the outer surface of the second flange 322 that is indented may be asymmetrical. That is, a greater volume material may be removed from a first side 504 of the distal end of the second flange 322 than a second side of the distal end of the second flange 506. Similarly, the area of the outer surface of the second flange that is indented is asymmetrical. That is, a greater volume of material is removed from a first side of the distal end of the first flange than a second side of the distal end of the first flange. This is because the pulleys of the second set of pulleys are not positioned directly below the pulleys of the first set of pulleys, such that their axes encompassed by the first plane 332. Instead, the pulleys are offset from the pulleys of the second set of pulleys as viewed from the second plane 346. The pulleys of the second set of pulleys may be positioned towards the first side 504 of the distal end of the second flange 322, and the corresponding first side of the distal end of the first flange. Thus, more material is removed from a first side of the flanges than from a second side of the flanges to complement the arrangement of the second set of pulleys with respect to the first set of pulleys.

In an alternative example, the second set of pulleys may be positioned directly below the pulleys of the first set of pulleys, such that their axes are encompassed by the first plane 332. In this example, the volume of material removed from the first side 504 of the distal end of the second flange 322 may be the same as the volume of material removed from the second side 506 of the distal end of the second flange. The same may be true for the first flange.

In a further example that is different to that which is illustrated in FIGS. 8 and 9, interference between the supporting body 304 and the second set of pulleys may be reduced by increasing the separation between the pulleys and the supporting body. This could be done by widening the diameter of the shaft so that there is more space along the first joint 310 for the components that rotate about that joint to be positioned. In other words, modifying the diameter of the shaft would provide greater clearance on either side of the supporting body 304 between the supporting body and the pulleys. For example, the separation d3 between the outer surface of the first flange 320 and the first pulley 324 (and a corresponding pulley of the second set of pulleys) may be increased to more than 0.1 mm. The separation d4 between the outer surface of the second flange 322 and the second pulley 326 (and a corresponding pulley of the second set of pulleys) may be increased so that it is greater than 0.1 mm. The advantage of this modification is that no material needs to be removed from the supporting body, which could result in a weakening of the supporting body.

The protrusions 342, 402 of FIGS. 4 and 8 may be coupled to the distal end to the shaft in a few different ways. In one example, the protrusion may form an integral part of the shaft. That is, the protrusion may be manufactured as part of the shaft, and the features of this component may be machined during production of the shaft in a similar manner to the first and second tines 306, 308. In an alternative example, the protrusion and the shaft 302 may be separate components. In this example, the protrusion may be connected to the shaft during manufacturing of the surgical instrument using any commonly known joining method. Such joining methods include but are not limited to welding, fastening using mechanical fasteners such as bolts or screws, and adhering using an adhesive solvent. The protrusion may be constructed from the same material as the shaft. The protrusion may alternatively be constructed from a different material to that of the shaft.

Figure 11:
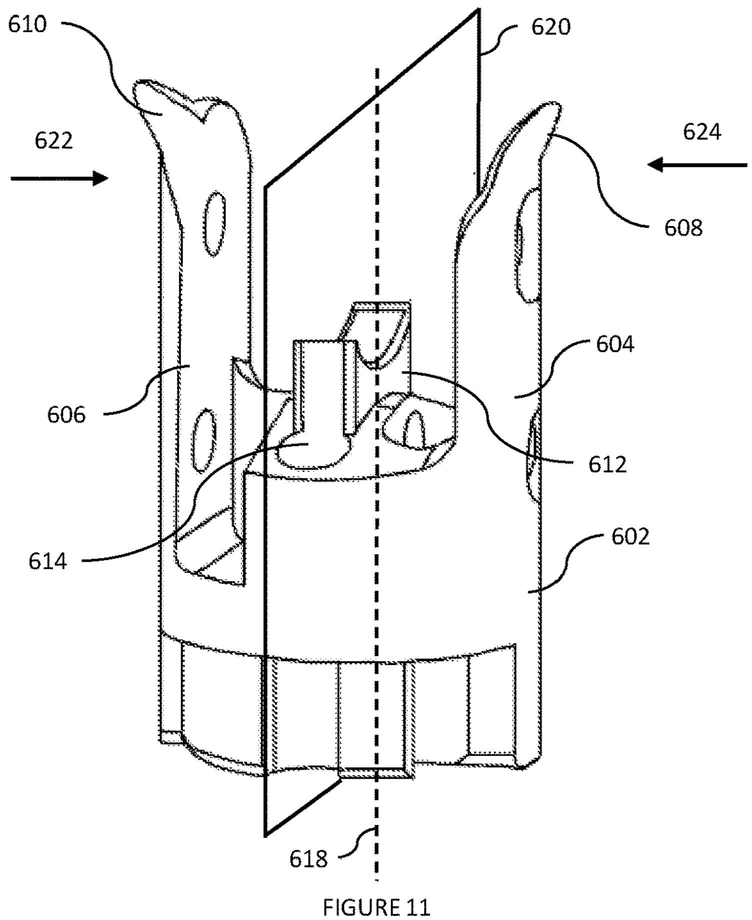
FIG. 11 illustrates an alternative configuration for the distal end of the shaft that may be used in the embodiment of the surgical instrument of FIG. 4.

FIG. 11 illustrates an alternative configuration of the distal end of the shaft 602 to the configuration illustrated in FIG. 6. This shaft 602 may replace shaft 302 in the surgical instrument illustrated in FIG. 4. As with shaft 302 illustrated in FIG. 6, the distal end of the shaft 602 comprises a first tine 604 and a second tine 606. The first and second tines extend away from the body of the shaft 602. That is, the first and second tines extend distally of the shaft 602. The first and second tines may extend in a direction that is parallel to the longitudinal axis 618 of the shaft. The first tine 604 of the shaft opposes the second tine 606. That is, the first tine 604 is located on an opposite side of the shaft to the second tine 606. The first tine 306 and the second tine 308 are spaced apart, which allows the supporting body, pulley arrangement and driving elements to be located between the tines.

Each of the tines 604, 606 comprises an appendage extending distally of the body of the tine. The first tine 604 comprises a first appendage 608 extending away from the body of the first tine, and towards the end effector. The second tine 606 comprises a second appendage 610 extending away from the body of the second tine, and towards the end effector. The first and second appendages 608, 610 are formed of material extruded from the bodies of their respective tines. The first and second appendages 608, 610 are smaller in size than the main bodies of their respective tines. The first and second appendages 608, 610 may be symmetrical about a plane 620 corresponding to plane 346 illustrated in FIG. 6. The plane 620 runs across the middle of the distal end of the shaft. The plane 620 is parallel to the longitudinal axis 618 of the shaft. In an alternative example, as is illustrated in FIG. 11, the first appendage 608 may extend in an opposing direction to that of the second appendage 610, relative to the plane 620. The appendages may be of any suitable shape. In FIG. 11 each of the first and second tines 604, 606 comprises one appendage 608, 610. In alternative examples, each of the first and second tines may comprise two, or more than two, appendages.

Appendages 608 and 610, as with the protrusions of the surgical instruments illustrated in FIGS. 4 and 8, act to limit the tilting of the supporting body when it is subjected to external forces. For example, if the supporting body is subjected to a force in a first direction 622, the supporting body will be rotated towards the first tine 604 and therefore towards the first appendage 608. Due to the principles of rotation, the supporting body will come into contact with the first appendage 608 sooner than it will come into contact with the body of the first tine 604. Thus, the tilting of the supporting body is limited more by the presence of the first appendage on the first tine than it would be if the first appendage were not present. Similarly, if the supporting body is subjected to a force in a second direction 624, the supporting body will be rotated towards the second tine 606 and therefore towards the first appendage 610. The supporting body will come into contact with the second appendage 610 sooner than it will come into contact with the body of the second tine 606. Thus, the tilting of the supporting body is limited more by the presence of the second appendage on the second tine than it would be if the second appendage were not present.

The shaft 602 comprises a protrusion 612 corresponding to protrusion 342 illustrated in FIG. 6. The shaft also comprises first and second holes 614 corresponding to the holes 330 illustrated in FIG. 6. Thus, the appendages 602, 604 of the shaft tines 306, 308 may be combined with the protrusion of FIG. 4. Alternatively, the appendages may be combined with the one or more protrusions 402 illustrated in FIG. 8. Additionally, or alternatively, the appendages may be combined with the modifications illustrated in FIGS. 9 and 10.

Figure 12:
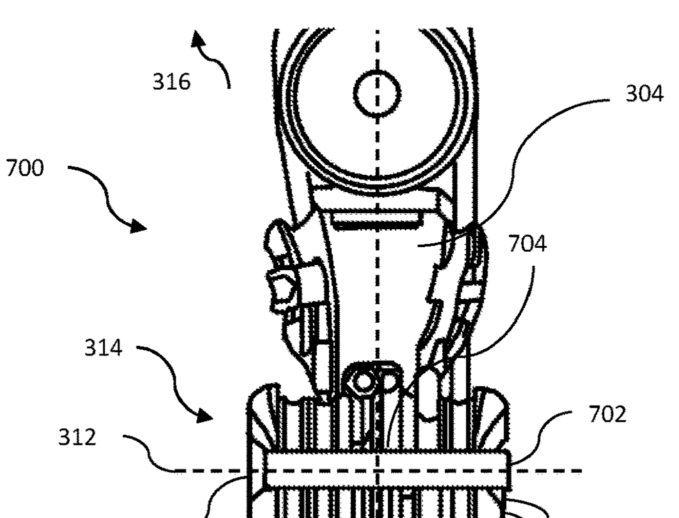
FIG. 12 illustrates a third configuration of a surgical instrument to be used with the surgical robot of FIG. 1.

A third exemplary configuration of a surgical instrument 700 to be used with the surgical robot of FIG. 1 is illustrated in FIG. 12. This surgical instrument 700 is substantially the same as the surgical instrument 300 illustrated in FIG. 4. The surgical instrument 700 comprises a supporting body 304 corresponding to the supporting body of the surgical instrument 300. The surgical instrument 700 also comprises a pulley arrangement, an end effector and a shaft that correspond to those of surgical instrument 300. The supporting body 304 of the surgical instrument 700 is connected to a distal end of the shaft 302 at a first end 314, and to the end effector at a second end 316.

As with the surgical instrument 300 of FIG. 4, the surgical instrument 700 of FIG. 12 comprises a first joint 702 which extends along a first axis 312 that is transverse to the longitudinal axis 318 of the shaft 302. As mentioned above, the first joint 702 comprises a pin connecting the supporting body 304 to the shaft 302. The pin of the first joint 702 is cylindrical in shape. The pin of the first joint has a length which extends along the first axis 312 and a circular cross-sectional area that is perpendicular to its length. The first axis 312 and the longitudinal axis 318 of the shaft are the same as the corresponding axes of the surgical instrument 300 illustrated in FIG. 4.

The supporting body 304 is connected to the distal end of the shaft by the pin of the first joint 702 such that the supporting body is configured to rotate about the first axis 312. In order to connect the pin of the first joint 702 to the supporting body 304, the supporting body comprises a channel 704 which extends through the first end 314 of the supporting body. In other words, the channel 704 of the supporting body is configured to house the pin of the first joint 702. Thus, when the surgical instrument is assembled, the pin of the first joint 702 passes through the first end 314 of the supporting body. The channel 704 is cylindrical in shape. The channel comprises a length which extends along the first axis 312 and a circular cross-sectional area that is perpendicular to its length.

The shaft 302 comprises a first tine 306 and a second tine 308. The first and second tines 306, 308 are the same as the corresponding tines of the surgical instrument 300 illustrated in FIG. 4. The opposing nature of the first and second tines 306, 308 enables the first end 314 of the supporting body, as well as an arrangement of pulleys and driving elements, to be located between the tines. The first tine 306 comprises a channel 706 that is configured to house a first end of the pin of the first joint 702. The second tine 308 comprises a channel 708 that is configured to house a second end of the pin of the first joint 702. The pulleys of the first set of pulleys also comprise corresponding channels through which the pin of the first joint 702 is configured to pass. When the surgical instrument 700 is assembled, the pin of the first joint passes through the channels of the first tine of the shaft, the second tine of the shaft the pulleys of the first set of pulleys and the first end of the supporting body.

The pin of the first joint 702 and the supporting body 304 are manufactured such that, before the pin of the first joint is connected to the supporting body, the diameter of the pin is greater than the diameter of the channel 704 of the supporting body. The diameter of the pin 702 bisects the circular cross-sectional area of the pin. The diameter of the channel 704 bisects the circular cross-sectional area of the channel. The difference between the diameter of the pin and the diameter of the channel may be no more than 1 millimetre. The increased diameter of the pin with respect to that of the channel 704 means that, when the pin is connected to the supporting body 304, there is an interference fit between the pin and the supporting body. An interference fit may otherwise be referred to as a press fit. An interference fit is a tight fit that restricts movement between the components that are secured together using this fit. The components are held together by strong frictional bonds between their interfacing surfaces. The pin may be assembled onto the supporting body 304 using a high pressure assembly device, such as a hydraulic ram, or any other suitable means.

By providing an interference fit between the pin of the first joint 702 and the channel 704 of the supporting body, movement of the supporting body with respect to the pin can be minimised. The strong frictional bonds between interfacing surfaces of these components means that the supporting body 304 will be held in place, relative to the pin, as the pin rotates relative to the distal end of the shaft 302. Thus, the interference fit further acts to minimise movement or tilting of the supporting body during rotation of the supporting body about the first axis 312, which could result in interaction between the supporting body and the pulley arrangement of the surgical instrument.

The interference fit illustrated in FIG. 12 may be combined with one or more features of the exemplary instrument arrangements illustrated in FIGS. 4 to 11 of the present application That is, a surgical instrument to be used with the surgical robot of FIG. 1 may comprise both a protrusion configured to interface with the flanges of the supporting body 304 (as illustrated in FIGS. 4-8) and an interference fit between the channel of its supporting body and the pin of the first joint 702 (as illustrated in FIG. 12). A surgical instrument may additionally or alternatively comprise appendages (as illustrated in FIG. 11). The surgical instrument may additionally or alternatively incorporate modified flanges on its supporting body (as illustrated in FIGS. 9 and 10). All of the modifications in FIGS. 4-12 may act together to reduce movement (e.g., tilting) the supporting body of the surgical instrument.

Figure 13:
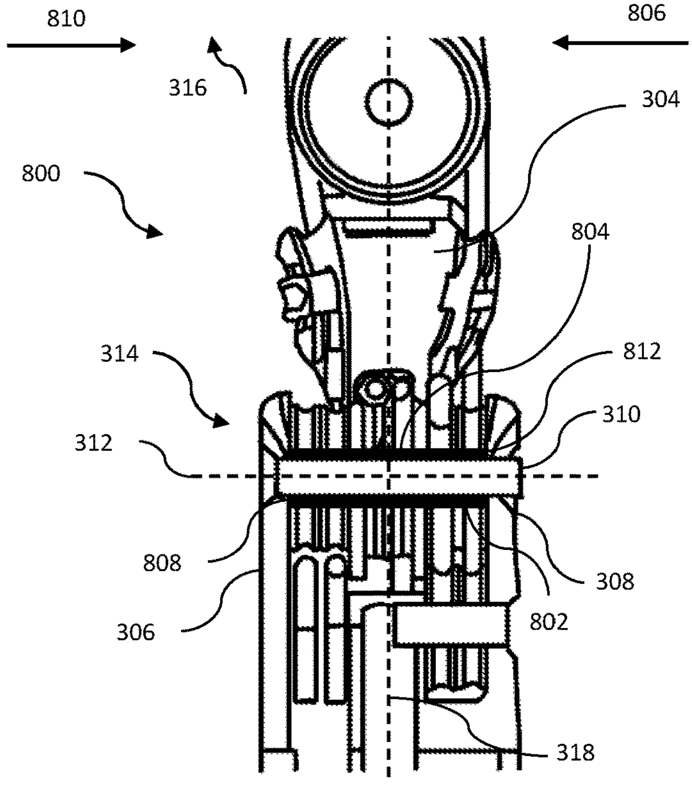
FIG. 13 illustrates a fourth configuration of a surgical instrument to be used with the surgical robot of FIG. 1.

An alternative example of the surgical instrument that is illustrated in FIG. 12 is illustrated in FIG. 13. The surgical instrument 800 is substantially the same as the surgical instrument 700 illustrated in FIG. 12. The surgical instrument 800 of FIG. 13 differs from that of FIG. 12 in that it comprises a hollow tube 802 that is rigidly connected to the first end 314 of its supporting body. The hollow tube 802 is configured, when the surgical instrument is assembled, to extend between the first and second tines 306, 308 of the distal end of the shaft 302. The pin of the first joint 310 is configured, when the surgical instrument is assembled, to pass through the hollow tube 802 such that rotation of the pin about the first axis 312 results in rotation of the supporting body 304 about the first axis. In other words, the hollow tube 802 provides a channel that ensures a connection between the supporting body 304 and the pin of the first joint 310. The hollow tube 802 may pass through a channel 804 in the first end of the supporting body 304. The hollow tube 802 may also pass through corresponding channels in each of the pulleys of the first set of pulleys. The channel 804 may correspond to channel 704 described with respect to FIG. 12. The hollow tube 802 is cylindrical in shape. The hollow tube 802 has a length that extends along the first axis 312 and a circular cross-sectional area that is perpendicular to that length.

The configuration of the surgical instrument illustrated in FIG. 13 is advantageous as it can also minimise movement between the supporting body 304 and the pin of the first joint. As is explained above, the hollow tube 802 extends between the first and second tines 306, 308 of the distal end of the shaft 302, and is rigidly connected to the supporting body 304. If the end effector element is subjected to a force in a first direction, indicated by reference numeral 806 in FIG. 13, a first end of the hollow tube 802 will come into contact with the first tine 306 of the shaft at a first location 808. This interference will limit the linear motion of the hollow tube 802 along the first axis 312 in the first direction 806. It will also limit motion of the supporting body that is rigidly connected to that tube in the first direction 806. The interference will also limit rotation of the supporting body 304 towards the first tine 306, thereby limiting interference of the supporting body 304 with the first pulleys of the first and second sets of pulleys.

Similarly, if the end effector element is subjected to a force in a second direction, indicated by reference numeral 810 in FIG. 13, a second end of the hollow tube 802 will come into contact with the second tine 308 of the shaft at a second location 812. This interference will limit the motion of the hollow tube 802 along the first axis 312 in the second direction 810. It will also limit motion of the supporting body 304 that is rigidly connected to that tube in the second direction 810. The interference will also limit rotation of the supporting body 304 towards the second tine 308, thereby limiting interference of the supporting body with the second pulleys of the first and second sets of pulleys.

The hollow tube 802 may form an integral part of the supporting body 304. That is, the hollow tube 802 may be manufactured as part of the supporting body 304. For example, hollow tube may be formed from circumferential flanges of the supporting body that extend on either side of the channel 804 along the first axis 312. A first circumferential flange may extend between the channel 804 and the first tine 306 of the shaft to match the width of the gap between the first tine and the channel. A second circumferential flange may extend between the channel 804 and the second tine 308 of the shaft to match the width of the gap between the second tine and the channel. Alternatively, the hollow tube 802 and the supporting body 304 may be separate components. The hollow tube 802 may be connected to the supporting body 304 during manufacturing of the surgical instrument using any commonly known joining method. Such joining methods include but are not limited to welding, fastening using mechanical fasteners such as bolts or screws, and adhering using an adhesive solvent. The hollow tube 802 may be constructed from the same material as the supporting body 304. The hollow tube 802 may alternatively be constructed from a different material to that of the supporting body 304. The hollow tube 802 may be connected to the pin of the first joint 310 using an interference fit.

As with the example of FIG. 12, the example of FIG. 13 may be combined with one or more of the exemplary instrument arrangements illustrated in FIGS. 4 to 11 of the present application That is, a surgical instrument to be used with the surgical robot of FIG. 1 may comprise both a protrusion configured to interface with the flanges of the supporting body 304 (as illustrated in FIGS. 4-8) and a hollow tube as illustrated in FIG. 13. A surgical instrument may additionally or alternatively comprise appendages (as illustrated in FIG. 11). The surgical instrument may additionally or alternatively incorporate modified flanges on its supporting body (as illustrated in FIGS. 9 and 10). The surgical instrument may additionally or alternatively comprise an interference fit between the pin of its first joint 310 and its hollow tube 802. All of the modifications in FIGS. 4-12 may act together to reduce movement (e.g., tilting) the supporting body of the surgical instrument.

Figure 14:
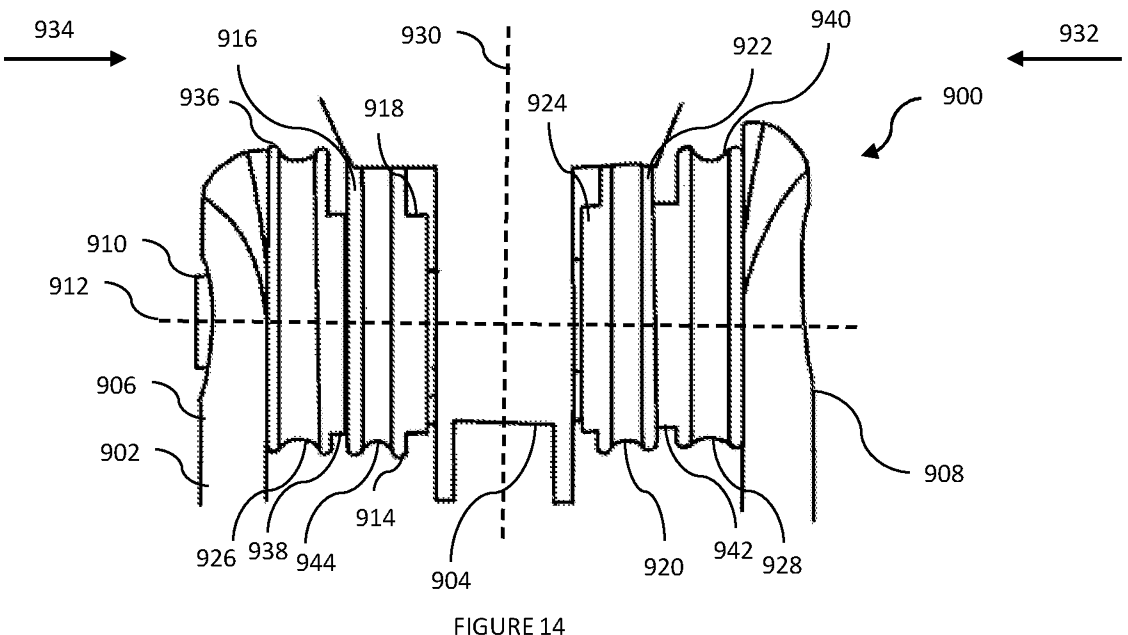
FIG. 14 illustrates a fifth configuration of a surgical instrument to be used with the surgical robot of FIG. 1.

A fifth configuration for a surgical robotic instrument is illustrated in FIG. 14. FIG. 14 illustrates a detailed portion of the surgical instrument 900 along the first joint 910 of the surgical instrument. The surgical instrument 900 has an end effector (not illustrated) that corresponds to the end effector described above with reference to FIGS. 4-13. The surgical instrument further comprises a supporting body 904 that corresponds to the supporting body 304 described with reference to FIGS. 4-13. The supporting body is connected to a distal end of a shaft 902 of the instrument at a first end and to the end effector at a second end. The first and second ends correspond to the first and second ends of the supporting body illustrated in FIG. 4.

The shaft 902 of the surgical instrument 900 also corresponds to the shaft (or shaft component) 302 described with reference to FIGS. 4-13. The distal end of the shaft 902 comprises a first tine 906 and a second tine 908. The first and second tines extend away (i.e., distally) from the body of the shaft 902 and towards the end effector. The first and second tines may extend in a direction that is parallel to the longitudinal axis 930 of the shaft. The first axis 912 and the longitudinal axis 930 of the shaft correspond to the respective axes of the surgical instrument 300 illustrated in FIG. 4. The first tine 906 of the shaft 902 opposes the second tine 908. That is, the first tine 906 is located on an opposite side of the shaft to the second tine 908. The first tine 906 and the second tine 908 are spaced apart. This enables an arrangement of pulleys and driving elements to be located between the tines. It also enables a first end of the supporting body 904 to be located between the tines.

The surgical instrument 900 comprises a first joint 910 which permits the end effector to rotate about a first axis 912. More specifically, the supporting body 904 is configured to rotate about the first axis 912 by means of the first joint 912.

The first joint 912 comprises a pin that is connected to the supporting body 904. The pin is configured to rotate relative to the shaft 902, thereby rotating the supporting body 904 relative to the shaft 902. The end effector is connected to the second end of the supporting body that opposes the first end of the supporting body. Thus, rotation of the supporting body 904 about the first axis 912 results in rotation of the end effector about the first axis 912. The first axis 912 is transverse to the longitudinal axis 930 of the shaft. The surgical instrument may further comprise second and third joints as described above with respect to FIG. 4.

The surgical instrument further comprises set of pulleys that are rotatable around the first axis 912. That is, the first set of pulleys rotates about the same axis as the first joint 910. The first set of pulleys may comprise only one pulley 914. Alternatively, the first set of pulleys may comprise two or more pulleys. In FIG. 14 the first pulley 914 is located between the supporting body 904 and the first tine 906 of the shaft. In an alternative example, the first pulley 914 may be located between the supporting body 904 and the second tine 908 of the shaft. The first pulley 914 of the first set of pulleys therefore faces an outer surface of the first end of the supporting body 904.

The first pulley 914 has a length which extends along the first axis 912 and more than one circular cross-sectional area that is perpendicular to its length. The first pulley comprises a first section 916 and a second section 918. The first section 916 of the first pulley is cylindrical in shape. The first section 916 of the first pulley has a first diameter. The first diameter 916 may be an outer diameter of the first section. The first diameter 916 may be consistent along the length of the first section 916. The second section 918 of the first pulley has a second diameter. The second diameter may be an outer diameter of the second section. Alternatively, the second diameter may be an inner diameter of the second section 918.

In one example, as illustrated in FIG. 14, the second section 918 of the first pulley is cylindrical in shape. That is, where the second diameter of the second section of the first pulley is an outer diameter of the second section, that second diameter is consistent along the length of the second section. In an alternative example, the second section 918 of the first pulley may be conical in shape. That is, the outer (or second) diameter of the second section may vary (i.e., increase or decrease) along the length of the second section. In this example, the second diameter of the second section 918 may be the outer diameter at an end of the second section furthest from the first section of the first pulley. Alternatively, the second diameter of the second section of the first pulley may be the outer diameter of the second section at an end of the second section closest to the first section of the first pulley. The second diameter of the second section may be the outer diameter of the second section at any suitable length along the second section. The first diameter of the first section and the second diameter of the second section of the first pulley are not the same. More specifically, the second diameter of the second section 918 is smaller than the first diameter of the first section 916. This is true irrespective of the location along the length of the second section at which the second diameter is measured.

The second section 918 of the first pulley 914 is configured to interfere with another component of the surgical instrument that rotates about the first joint. For example, the second section 918 of the first pulley may face an outer surface of the first end of the supporting body 904. In other words, the second section 918 of the first pulley may be adjacent to the supporting body 904. The first section 916 of the first pulley faces in an opposing direction to the second section of the first pulley, and so may face towards the first tine 906 of the surgical instrument. In other words, the first section 916 of the first pulley may be located between the second section 918 of the pulley and the first tine 906. The second section 918 of the first pulley may be configured to interfere with the supporting body 904 so as to restrict movement of the supporting body towards the first pulley. That is, if the supporting body 904 is moved (e.g., rotated) towards the first pulley 914 in a first direction 932 (illustrated in FIG. 14), the second section 918 of the first pulley will interfere with the corresponding outer surface of the supporting body. The interference between the second section 918 of the first pulley and the supporting body 904 will limit the degree of movement (e.g., rotation) that can be achieved by the supporting body. In another example, the second section 918 of the first pulley may be configured to interfere with another pulley of the surgical instrument so as to restrict movement of the supporting body towards the first pulley. In this example the first section of the first pulley is also configured to interfere with the supporting body so as to restrict movement of the supporting body.

The purpose of the first pulley 914 is to route at least one driving element of the second pair of driving elements B1, B2 that is configured to drive a joint of the surgical instrument. In other words, at least one driving element of the second pair of driving elements is routed around the first pulley. The second pair of driving elements is described above with respect to FIGS. 2 and 4. The first pulley 914 may be configured to route a first driving element B1 of the second pair of driving elements around it. The first section 916 of the pulley may comprise a groove 944 that extends around the circumference of the first section of the first pulley. The groove 944 provides a recess that is stepped back from the outer surface of the first section 916. The groove 944 may permit a driving element of the second pair of driving elements to be routed around the pulley. Thus, the first section 914 of the first pulley is the section of the pulley that is configured to route one or more driving elements of the surgical instrument.

The addition of the second section 918 to the first pulley 914 increases the overall width of the pulley. The increase in width means that there is less free space along the pin of the first joint 910 between the first tine 906 of the shaft, the first pulley 914 and the supporting body 904. So, the supporting body 904 has limited space along which it is able to move (e.g., linearly) before it comes into contact with the second section of the first pulley. This reduction in free space limits the degree of tilting and/or linear movement of the supporting body relative to the first joint 910.

The width of the second section 918 of the first pulley may be sufficiently large with respect to the width of the first section 916 of the pulley, in order to ensure that there is a sufficient reduction in free space along the length of the pin of the first joint. For example, the ratio of the width of the second section relative to the first section may be at least 2:5. Preferably the ratio of the width of the second section relative to the first section is between 1:3 and 1:5. This ensures that the movement of the supporting body is sufficiently limited. The overall width of the first pulley may be at least 0.4 mm. A suitable range of widths for the first pulley may be between 0.4 mm and 1.4 mm. In a specific example, the width of the first pulley may be 0.7 mm. The shaft 902 of the surgical instrument may have an outer diameter of between 5 and 7 mm. In a specific example, the outer diameter of the shaft 902 may be 6.8 mm. The selection of an outer diameter within this range ensures that the shaft is able to be articulated and positioned with ease during surgical procedures, whilst also ensuring that there is sufficient space for a pulley arrangement incorporating pulleys with increased widths. The outer diameter of the shaft is also kept small to reduce the size of incisions created by the instrument during surgery, which provides benefits in patient recovery.

The configuration of the instrument illustrated in FIG. 14 is advantageous because the second section 918 of the first pulley acts to limit movement (e.g., tilting) of the supporting body 904 when it is subjected to external forces. As the second section 918 of the first pulley increases the overall width of the pulley, the degree to which the supporting body 904 is able to move (e.g., tilt) before it is stopped by the first pulley is reduced. This means that the driving element(s) that are driven around the first pulley will not be obstructed by the supporting body 904 and the efficiency of the end effector element that is driven by these driving element(s) can be maintained. The diameter of the second section 918 of the first pulley is smaller than the diameter of the first section 916 of the pulley. Thus, the cross-sectional area of the second section 918 of the first pulley is smaller than the cross-sectional area of the first section of the pulley. This means that the frictional forces experienced when the second section 918 of the first pulley interferes with either the supporting body 904 or another pulley of the surgical instrument are reduced. Consequently, the impact of this interference on the rotational efficiency of the first pulley is minimised, which is beneficial for articulation of the surgical instrument. To minimise the frictional forces, the outer diameter of the second section of the first pulley may be less than or equal to 3 mm. In a preferred example, the outer diameter of the second section of the first pulley may be 2 mm. The outer diameter of the second section of the first pulley may be half of the diameter of the first section of the pulley.

Each of the first and second sections of the first pulley comprises an inner diameter in addition to an outer diameter. The inner diameter of the first section 916 may be substantially the same as the outer diameter of the pin of the first joint 910. In one example, the inner diameter of the second section 918 is also substantially the same as the outer diameter of the pin of the first joint 910. In this example, the inner diameter of the first section 916 is the same as the inner diameter of the second section 918. In another example, the inner diameter of the second section 918 is greater than the inner diameter of the first section 916. This means that the inner diameter of the second section is larger than is necessary to house the pin of the first joint 910. An advantage of the inner diameter of the second section 918 being configured in this way is that the surface area of the first pulley that comes into contact with the supporting body 904 is further reduced. Thus, the frictional forces between the first pulley 914 and the supporting body 904 are further reduced.

In addition to the first pulley 914, the first set of pulleys may further comprise a second pulley 920. The purpose of the second pulley 920 is to route at least one driving element of the third pair of driving elements C1, C2 that is configured to drive a joint of the surgical instrument. In other words, at least one driving element of the third pair of driving elements is routed around the second pulley. The second pulley 920 may be configured to route the first driving element C1 of the third pair of driving elements around it. As with the first pulley 914, the second pulley 920 comprises a first section 922 with a first diameter and a second section 924 with a second diameter that is smaller than the first diameter. The first pulley 914 may face a first outer surface of the supporting body 904, so the second pulley 920 may correspondingly face a second outer surface of the supporting body. The first and second pulleys are located on opposing sides of the supporting body 904. The first and second pulleys are also located on opposite sides of the first joint 910 relative to the longitudinal axis 930 of the shaft. The second pulley 920 may comprise all of the features described above with respect to the first pulley 914.

The second section 924 of the second pulley 920 is configured to interfere with another component of the surgical instrument that rotates about the first joint. For example, the second section 924 of the second pulley 920 may be configured to interfere with the supporting body 904 so as to restrict movement of the supporting body towards the second pulley. That is, if the supporting body 904 is moved (e.g., rotated) towards the second pulley 920 in a second direction 934 (illustrated in FIG. 14), the second section 924 of the second pulley will interfere with the corresponding outer surface of the supporting body. The interference between the second section 924 of the second pulley and the supporting body will limit the degree of movement (e.g., rotation) that can be achieved by the supporting body. In another example, the second section 924 of the second pulley 920 may be configured to interfere with another pulley of the surgical instrument so as to restrict movement of the supporting body towards the second pulley. In this example the first section of the second pulley is configured to interfere with the supporting body so as to restrict movement of the supporting body. In other words, the second pulley 920 has the same purpose as the first pulley 914, but on an opposing side of the supporting body 904.

The first set of pulleys may further comprise a third pulley 926 located between the first pulley 914 and the first tine 906 of the shaft. The purpose of the third pulley is to route a second driving element of the second pair of driving elements B1, B2 around it. As with the first and second pulleys, the third pulley may comprise a first section 936 with a first diameter and a second section 938 with a second diameter that is smaller than the first diameter. The third pulley 926 may comprise all of the features described above with respect to the first and second pulleys. Thus, the third pulley may only differ from the first and second pulleys in its location. The second section 938 of the third pulley may face a section of the first pulley. For example, the second section 938 of the third pulley may face the first section 916 of the first pulley. The second section 938 of the third pulley may therefore be configured to interfere with the first pulley 914 so as to restrict movement of the first pulley 914 towards the third pulley 926. Alternatively, or additionally, the second section 918 of the first pulley may face a section of the third pulley 926. For example, the second section 918 of the first pulley may face the first section 936 of the third pulley. In this example, second section 938 of the third pulley faces the first tine 906 of the shaft. The first section of the third pulley is configured to interfere with the first pulley so as to restrict movement of the first pulley towards the third pulley.

As the second section of the third pulley increases the overall width of the third pulley, the degree to which the second pulley 920 is able to move (e.g., tilt) before it is stopped by the third pulley is reduced. This ultimately also limits movement of the supporting body toward the third pulley 926 (and the second pulley 920), which means that the driving element(s) that are routed around the second pulley will not be obstructed by the supporting body 904 and the efficiency of the end effector element that is driven by these driving element(s) can be maintained.

The diameter of the second section 938 of the third pulley is smaller than the diameter of the first section 916 of the third pulley. This means that the frictional forces experienced when the third pulley 926 interfaces with the first pulley 914 or the first tine 906 are reduced. Consequently, the impact of this interference on the rotational efficiency of both the first and third pulleys is minimised, which is beneficial for articulation of the surgical instrument.

The first set of pulleys may further comprise a fourth pulley 928 located between the second pulley 920 and the second tine 908 of the shaft. The purpose of the fourth pulley is to route a second driving element of the third pair of driving elements C1, C2 around it. The fourth pulley may comprise a first section 940 with a first diameter and a second section 942 with a second diameter that is smaller than the first diameter. The fourth pulley 928 may comprise all of the features described above with respect to the first, second and third pulleys. Thus, the fourth pulley may only differ from the first, second and third pulleys in its location. The second section 942 of the fourth pulley may face a section of the second pulley. For example, the second section of the fourth pulley may face the first section 922 of the second pulley. The second section 942 of the fourth pulley may therefore be configured to interfere with the second pulley 920 so as to restrict movement of the second pulley 920 towards the fourth pulley 928. Alternatively, or additionally, the second section of the second pulley may face a section of the fourth pulley 928. For example, the second section of the second pulley may face the first section 942 of the fourth pulley. In this example, second section 942 of the fourth pulley faces the second tine 908 of the shaft. The first section of the fourth pulley is configured to interfere with the second pulley so as to restrict movement of the second pulley towards the fourth pulley.

As the second section of the fourth pulley increases the overall width of the fourth pulley, the degree to which the first pulley 914 is able to move (e.g., tilt) before it is stopped by the fourth pulley is reduced. This ultimately also limits movement of the supporting body toward the fourth pulley 928 (and the second pulley 920), which means that the driving element(s) that are routed around the second pulley will not be obstructed by the supporting body 904 and the efficiency of the end effector element that is driven by these driving element(s) can be maintained.

The diameter of the second section of the fourth pulley is smaller than the diameter of the first section of the fourth pulley. This means that the frictional forces experienced when the fourth pulley 928 interfaces with the second pulley 920 or the second tine 908 are reduced. Consequently, the impact of this interference on the rotational efficiency of both the fourth and second pulleys is minimised, which is beneficial for articulation of the surgical instrument.

The second section of each pulley of the pulley arrangement illustrated in FIG. 14 may be provided by means of a boss. A boss is defined as a protruding feature on a mechanical object that is used to locate that object against another object.

Figure 15:
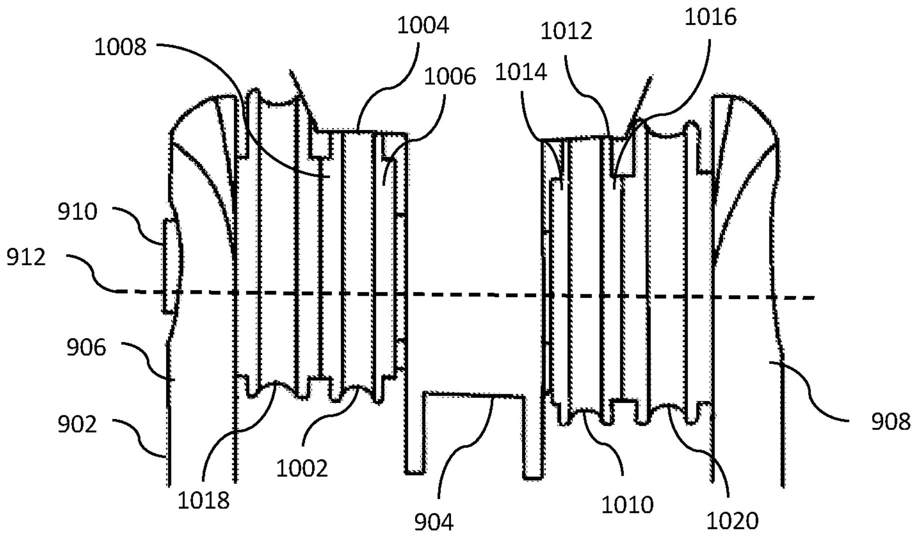
FIG. 15 illustrates a sixth configuration of a surgical instrument to be used with the surgical robot of FIG. 1.

A further development of the pulley arrangement illustrated in FIG. 14 is displayed in FIG. 15. The arrangement of FIG. 15 is substantially the same as the arrangement illustrated in FIG. 14. The surgical instrument of FIG. 15 also comprises a first pulley 1002 with first and second sections 1004, 1006. The first section of the first pulley may comprise a groove as described above with respect to FIG. 14. The first pulley 1002 of FIG. 15 differs from the first pulley 914 of FIG. 14 in that it further comprises a third section 1008. The third section 1008 of the first pulley comprises a third diameter that is smaller than the diameter of the first section 1002 of the pulley. The purpose of the third section 1008 of the first pulley is to interfere with either first tine 906 of the shaft, the supporting body 904 or the third pulley 1018. The component that the third section 1008 interferes with is dependent on whether or not the pulley arrangement comprises a third pulley. The third section 1008 of the first pulley is located on an opposing side of the first section 1004 of the pulley to the second section 1006. The third section 1008 of the first pulley may be located between the second section 1006 of the first pulley and the first tine 906.

The third section 1008 of the first pulley being configured to restrict movement of the supporting body towards the first tine. That is, the addition of the third section 1008 to the first pulley further increases the width of the pulley, which further reduces the space along the pin of the first joint 910 between the first tine 906 of the shaft, the first pulley 914 and the supporting body 904. This reduction in free space further limits the degree of tilting and/or linear movement of the supporting body relative to the first joint 910 from the example illustrated in FIG. 14. At the same time, the decreased diameter of the third section of the pulley relative to the first section of the pulley means that the cross-sectional area of the third section of the first pulley 1002 is smaller than the cross-sectional area of the first section of the pulley. This means that the frictional forces experienced when the third section of the pulley interferes with either the first tine 906, the supporting body 904 or the third pulley 1018 are reduced. Consequently, the impact of the interference on the rotational efficiency of the both the first and third pulleys is minimised, which is beneficial for articulation of the surgical instrument. In one example, the diameter of the third section 1008 is the same as the diameter of the second section 1006. This means that the reduction in frictional force is uniform on both sides of the pulley.

The surgical instrument may further comprise second 1010, third 1018 and fourth 1020 pulleys with features corresponding to those of the first pulley. The similarities between the second, third and fourth pulleys are the same as those described above with respect to the pulley arrangement of FIG. 14, apart from that the pulleys of FIG. 15 comprise an additional (third) section in addition to the first and second sections of those of FIG. 14. The advantage of the use of the pulleys illustrated in FIG. 15 comprising second and third sections with reduced diameters is that, whilst the width of the pulleys is increased, the friction between each pulley and the other components of the surgical instrument with which it interacts is reduced on both sides on the pulley. That is, in addition to reducing frictional forces between the first pulley and the supporting body, frictional forces between the first pulley and either the third pulley, the supporting body or the first tine of the surgical instrument may also be reduced. The same is true of the second, third and fourth pulleys and the components adjacent to those pulleys. Thus, the rotational efficiencies of the pulleys of FIG. 15 are further optimised over those illustrated in FIG. 14.

As has been summarised before, the movement of the supporting body 904 that is limited by the pulley arrangement of FIGS. 14 and 15 may include linear movement along the pin of the first joint 910. This movement may additionally or alternatively include rotation about a rotational axis that is transverse to both the first axis 912 of the first joint 910 and the longitudinal axis 903 of the shaft. As with the example illustrated in FIG. 14, the second and third sections of each pulley of the pulley arrangement illustrated in FIG. 15 may be provided by means of a boss. That is, each pulley of the pulley arrangement illustrated in FIG. 15 may comprise a first boss forming its second section and a second boss forming its third section.

The exemplary pulley arrangements illustrated in FIGS. 14 and 15 may be combined with one or more of the features of the exemplary instrument arrangements illustrated in FIGS. 4 to 12 of the present application. That is, a surgical instrument to be used with the surgical robot of FIG. 1 may comprise both a pulley arrangement as illustrated in FIG. 14 or FIG. 15 as well as a protrusion coupled to the distal end of the shaft configured to interface with the flanges of the supporting body 304 (as illustrated in FIGS. 4-8). Alternatively or additionally to this, the arrangement illustrated in FIGS. 14 and 15 may be combined with an arrangement as illustrated in FIG. 12, in which there is an interference fit between a channel of the supporting body and the pin of the first joint. A surgical instrument may additionally or alternatively comprise a hollow tube as illustrated in FIG. 13, and/or appendages as illustrated in FIG. 11. The surgical instrument may additionally or alternatively incorporate modified flanges on its supporting body as illustrated in FIGS. 9 and 10. All of the modifications in FIGS. 4-15 may act together to reduce movement (e.g., tilting) the supporting body of the surgical instrument.

The configuration of pulleys described above, wherein each pulley comprises a first section and a second section, has been described with reference to the first set of pulleys of a surgical instrument. However, it is also possible for the pulleys of the second set of pulleys of the instrument to be configured in this way. Alternatively, the pulleys of a further set of pulleys of the surgical instrument could be configured in this way. That is, a robotic surgical instrument may generally comprise a pulley arrangement with a first pulley and a second pulley adjacent to the first pulley. The first or second pulley comprises a first section with a first diameter and a second section with a second diameter that is smaller than the first diameter. The second section of the first or second pulley may be configured to restrict movement of the other one of the first or second pulley. The advantage of configuring the pulleys of any of the sets of pulleys in the instrument in this way is that the movement (e.g., tilting) of the pulleys, and other components, is restricted about their respective joint. Thus, the overall stability of the surgical instrument is improved. Any other joint in the surgical robot arm may comprise at least a first and second pulley as described above. The joint may further comprise third and fourth pulleys configured to interact similarly to the first and second pulleys as described above.

The values of the dimensions given in the examples above are given by way of example only, and in other examples the dimensions may have other suitable values. The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description, it will be evident to a person skilled in the art that various modifications may be made within the scope of the invention.

The invention claimed is:

1. A robotic surgical instrument comprising:
an end effector;
a shaft component;
a supporting body connected to a distal end of the shaft component at a first end and to the end effector at a second end, the supporting body comprising first and second flanges extending from the first end into the shaft component;
a pulley facing an outer surface of the first flange; and
a protrusion located within the distal end of the shaft component and extending towards the end effector, and configured to interface with an interfacing surface of one of the first or second flanges when the supporting body is moved towards the pulley;
wherein the separation between the outer surface of the first flange and the pulley is greater than the separation between said interfacing surface of one of the first or second flanges and the protrusion;
wherein when the instrument is in a neutral position in which no external forces are acting on the instrument, the separation between the outer surface of the first flange and the pulley is a non-zero distance, and the separation between the interfacing surface of the one of the first or second flanges and the protrusion is a non-zero distance, such that when the instrument is moved from the neutral position by the supporting body moving towards the pulley, the protrusion interfaces with the interfacing surface of the one of the first or second flanges and the first flange is prevented from coming into contact with the pulley.

2. The robotic surgical instrument of claim 1, wherein the protrusion is located between the first and second flanges and the said one of the first or second flanges is the second flange.

3. The robotic surgical instrument of claim 2, wherein said interfacing surface is an inner surface of the second flange.

4. The robotic surgical instrument of claim 2, wherein the pulley facing the outer surface of the first flange is a first pulley and the robotic surgical instrument further comprises a second pulley facing an outer surface of the second flange, the protrusion being configured to interface with an inner surface of the first flange when the supporting body is moved towards the second pulley, and wherein the separation between the outer surface of the second flange and the second pulley is greater than the separation between the inner surface of the first flange and the protrusion.

5. The robotic surgical instrument of claim 4, wherein when the instrument is in a neutral position, the separation between the outer surface of the first flange and the first pulley is the same as the separation between the outer surface of the second flange and the second pulley.

6. The robotic surgical instrument of claim 2, wherein the separation between the inner surface of the first flange and the inner surface of the second flange is 0.1 mm greater than the width of the protrusion, and/or when the instrument is in an equilibrium position, the separation between the inner surface of the first flange and the protrusion is 0.05 mm, and/or when the instrument is in an equilibrium position, the separation between the inner surface of the second flange and the protrusion is 0.05 mm.

7. The robotic surgical instrument of claim 1, wherein the protrusion is located between the first flange and the pulley, said one of the first or second flanges is the first flange, and said interfacing surface is the outer surface of the first flange.

8. The robotic surgical instrument of claim 7, wherein the pulley facing the outer surface of the first flange is a first pulley and the robotic surgical instrument further comprises a second pulley facing an outer surface of the second flange, and wherein the robotic surgical instrument further comprises a second protrusion located within the distal end of the shaft component and extending towards the end effector, the second protrusion being located between the second flange and the second pulley and configured to interface with the outer surface of the second flange when the supporting body is moved towards the second pulley, wherein the separation between the outer surface of the second flange and the second pulley is greater than the separation between said outer surface of the second flange and the protrusion.

9. The robotic surgical instrument of claim 1, wherein the supporting body is configured to rotate at a first joint about a first axis which is transverse to a longitudinal axis of the shaft component, the first joint comprising a pin connected to the supporting body and configured to rotate relative to the shaft component, wherein the supporting body comprises a channel extending through its first end and configured to house the pin of the first joint.

10. The robotic surgical instrument of claim 9, wherein the shaft component further comprises opposing first and second tines that extend distally of the shaft component, the robotic surgical instrument further comprising a hollow tube rigidly connected to the first end of the supporting body and configured to pass through the channel extending through the first end of the supporting body between the first and second tines of the shaft component, the pin of the first joint being configured to pass through the hollow tube such that rotation of the first joint about the first axis results in rotation of the supporting body about the first axis.

11. The robotic surgical instrument of claim 9, wherein the pulley is configured to rotate at the first joint about the first axis.

12. The robotic surgical instrument of claim 9, further comprising a first pair of driving elements configured to drive the first joint of the instrument, the first pair of driving elements comprising a first driving element extending through a first hole in the distal end of the shaft component and a second driving element extending through a second hole in the shaft component, wherein the length of the protrusion extends along the shaft component and along the length of the separation between the first hole and the second hole.

13. The robotic surgical instrument of claim 1, wherein the geometry of the distal end of the protrusion is complementary to the geometry of the first end of the supporting body, and/or a distal surface of the protrusion has a semi-elliptical profile.

14. The robotic surgical instrument of claim 1, wherein a length of the protrusion across the shaft component is between 2.6 mm and 3 mm.

15. The robotic surgical instrument of claim 1, wherein the length of the protrusion is aligned with an axis running across the middle of the shaft component.

16. The robotic surgical instrument of claim 1, wherein the width of each of the first flange and the second flange is 0.3 mm.

17. The robotic surgical instrument of claim 1, wherein an area of the outer surface of the first flange is indented asymmetrically at a distal end.

18. The robotic surgical instrument of claim 1, wherein an area of the outer surface of the second flange is indented at a distal end.

19. The robotic surgical instrument of claim 18, wherein the area of the outer surface of the second flange that is indented is asymmetrical.

20. The robotic surgical instrument of claim 1, wherein the shaft component further comprises opposing first and second tines that extend distally of the shaft component, each of the first and second tines comprising an appendage extending distally of its respective tine, each appendage being configured to interface with the supporting body when the supporting body is subjected to a force that moves it towards the respective tine of that appendage.

* * * * *